(12) United States Patent
Davidson et al.

(10) Patent No.: US 9,993,602 B2
(45) Date of Patent: Jun. 12, 2018

(54) FLOW REGULATING INHALER DEVICE

(71) Applicant: Syqe Medical Ltd., Te-Aviv (IL)

(72) Inventors: Perry Davidson, Tel-Aviv (IL); Aaron Schorr, Bat-Yam (IL); Binyamin Schwartz, Sde Eliezer (IL)

(73) Assignee: Syqe Medical Ltd., Tel-Aviv (IL)

( * ) Notice: Subject to any disclaimer, the term of this patent is extended or adjusted under 35 U.S.C. 154(b) by 0 days. days.

(21) Appl. No.: 15/312,647

(22) PCT Filed: Jun. 30, 2015

(86) PCT No.: PCT/IL2015/050678
§ 371 (c)(1),
(2) Date: Nov. 20, 2016

(87) PCT Pub. No.: WO2016/001926
PCT Pub. Date: Jan. 7, 2016

(65) Prior Publication Data
US 2017/0203058 A1  Jul. 20, 2017

Related U.S. Application Data

(60) Provisional application No. 62/164,710, filed on May 21, 2015, provisional application No. 62/086,208,
(Continued)

(51) Int. Cl.
*A61M 15/00* (2006.01)
*A61M 11/04* (2006.01)
(Continued)

(52) U.S. Cl.
CPC ...... *A61M 15/002* (2014.02); *A61M 15/0001* (2014.02); *A61M 15/005* (2014.02);
(Continued)

(58) Field of Classification Search
CPC .... A61M 11/02; A61M 11/04; A61M 11/041; A61M 11/042; A61M 11/044;
(Continued)

(56) References Cited

U.S. PATENT DOCUMENTS 3,203,432 A    8/1965  Green et al.
3,894,544 A    7/1975  Egri
(Continued)

FOREIGN PATENT DOCUMENTS

AU    199641966    5/1996
EP     2292108     3/2011
(Continued)

OTHER PUBLICATIONS

Official Action dated Apr. 20, 2017 From the US Patent and Trademark Office Re. U.S. Appl. No. 15/382,819. (30 pages).
(Continued)

*Primary Examiner* — Colin W Stuart

(57) ABSTRACT

An inhaler device for pulmonary delivery of at least one substance from a drug dose cartridge to an inhaling user, including: a first conduit for conducting a carrier airflow to a proximal opening of a mouthpiece for use by the user; a holder configured to position the dose cartridge within the carrier airflow; and a second conduit for conducting a shunting airflow to the mouthpiece without passing through the dose cartridge position. A controller connected to a valve controls a rate of carrier airflow, for example by controlling the shunting airflow, based on a sensor indication of airflow rate and a target airflow profile.

28 Claims, 18 Drawing Sheets

Related U.S. Application Data filed on Dec. 2, 2014, provisional application No. 62/085,772, filed on Dec. 1, 2014, provisional application No. 62/035,588, filed on Aug. 11, 2014, provisional application No. 62/019,225, filed on Jun. 30, 2014.

(51) Int. Cl.
    *A24F 47/00* (2006.01)
    *A61M 11/02* (2006.01)

(52) U.S. Cl.
    CPC .... *A61M 15/0013* (2014.02); *A61M 15/0015* (2014.02); *A24F 47/008* (2013.01); *A61M 11/02* (2013.01); *A61M 11/041* (2013.01); *A61M 11/042* (2014.02); *A61M 15/0021* (2014.02); *A61M 15/0091* (2013.01); *A61M 2205/3334* (2013.01); *A61M 2205/3368* (2013.01)

(58) Field of Classification Search
    CPC A61M 11/045; A61M 11/047; A61M 11/048; A61M 15/00; A61M 15/0001; A61M 15/0013; A61M 15/002; A61M 15/0021; A61M 15/0045; A61M 15/0086; A61M 15/0088; A61M 15/0091; A61M 15/0096; A61M 15/005
    USPC ............ 128/203.12, 203.14, 203.15, 203.17, 128/203.22, 203.24, 203.25
    See application file for complete search history.

(56) References Cited

U.S. PATENT DOCUMENTS

| | | | |
|---|---|---|---|
| 4,735,358 A | 4/1988 | Morita et al. | |
| 4,966,171 A | 10/1990 | Serrano et al. | |
| 4,969,477 A | 11/1990 | Yagisawa | |
| 5,301,666 A | 4/1994 | Lerk et al. | |
| 5,388,594 A | 2/1995 | Counts et al. | |
| 5,404,871 A | 5/1995 | Goodman et al. | |
| 5,479,948 A | 1/1996 | Counts et al. | |
| 5,649,554 A | 7/1997 | Sprinkel et al. | |
| 5,655,520 A | 8/1997 | Howe et al. | |
| 5,792,057 A | 8/1998 | Rubsamen et al. | |
| 6,703,418 B2 | 3/2004 | Plasse | |
| 6,761,164 B2 | 7/2004 | Amirpour et al. | |
| 7,088,914 B2 * | 8/2006 | Whittle .................. | A61K 9/007 128/203.27 |
| 7,169,378 B2 | 1/2007 | Rabinowitz et al. | |
| 7,287,530 B1 | 10/2007 | Stuart | |
| 7,537,005 B2 | 5/2009 | Dave | |
| 7,987,846 B2 | 8/2011 | Hale et al. | |
| 8,235,037 B2 | 8/2012 | Hale et al. | |
| 8,408,200 B2 | 4/2013 | Clark et al. | |
| 8,615,407 B2 | 12/2013 | Hyde et al. | |
| 2001/0027789 A1 | 10/2001 | Goede et al. | |
| 2002/0168322 A1 | 11/2002 | Clark et al. | |
| 2003/0037785 A1 | 2/2003 | Sonntag | |
| 2003/0041859 A1 | 3/2003 | Abrams et al. | |
| 2003/0062042 A1 | 4/2003 | Wensley et al. | |
| 2003/0168057 A1 * | 9/2003 | Snyder .............. | A61M 15/0065 128/200.21 |
| 2003/0200964 A1 | 10/2003 | Blakley et al. | |
| 2004/0045567 A1 | 3/2004 | Lewis et al. | |
| 2004/0069798 A1 | 4/2004 | Grey et al. | |
| 2004/0084044 A1 | 5/2004 | Childers et al. | |
| 2004/0099266 A1 * | 5/2004 | Cross .................. | A61M 11/041 128/203.12 |
| 2004/0192760 A1 | 9/2004 | Whittle et al. | |
| 2005/0063686 A1 | 3/2005 | Whittle et al. | |
| 2005/0126562 A1 | 6/2005 | Rabinowitz et al. | |
| 2005/0244521 A1 | 11/2005 | Strickland et al. | |
| 2005/0268909 A1 | 12/2005 | Bonney et al. | |
| 2005/0268911 A1 | 12/2005 | Cross et al. | |
| 2006/0102175 A1 | 5/2006 | Nelson | |
| 2006/0120962 A1 | 6/2006 | Rabinowitz et al. | |
| 2006/0157491 A1 | 7/2006 | Whittle et al. | |
| 2006/0167084 A1 | 7/2006 | Dudley | |
| 2006/0258738 A1 | 11/2006 | Dieterich | |
| 2007/0072938 A1 | 3/2007 | Rose | |
| 2007/0122353 A1 | 3/2007 | Hale et al. | |
| 2007/0074721 A1 | 4/2007 | Harmer et al. | |
| 2007/0102013 A1 | 5/2007 | Adams et al. | |
| 2007/0209661 A1 | 9/2007 | Smyth et al. | |
| 2007/0240712 A1 | 10/2007 | Fleming et al. | |
| 2007/0286816 A1 | 12/2007 | Hale et al. | |
| 2008/0072898 A1 | 3/2008 | Quoniam | |
| 2008/0078382 A1 | 4/2008 | LeMahieu et al. | |
| 2008/0140250 A1 | 6/2008 | Dave | |
| 2008/0176885 A1 | 7/2008 | Holtman et al. | |
| 2008/0181942 A1 | 7/2008 | Zajicek | |
| 2008/0299048 A1 | 12/2008 | Hale et al. | |
| 2008/0311176 A1 | 12/2008 | Hale et al. | |
| 2009/0084865 A1 * | 4/2009 | Maharajh ............. | A61M 11/041 239/1 |
| 2009/0151722 A1 | 6/2009 | Eason et al. | |
| 2009/0197941 A1 | 8/2009 | Guy et al. | |
| 2009/0241949 A1 | 10/2009 | Smutney et al. | |
| 2009/0293888 A1 | 12/2009 | Williams et al. | |
| 2009/0308390 A1 | 12/2009 | Smutney et al. | |
| 2009/0320836 A1 | 12/2009 | Baker, Jr. | |
| 2010/0012118 A1 | 1/2010 | Storz | |
| 2010/0035978 A1 | 2/2010 | Guy et al. | |
| 2010/0154795 A1 | 6/2010 | Pentafragas | |
| 2010/0168228 A1 | 7/2010 | Bose | |
| 2010/0181387 A1 | 7/2010 | Zaffaroni et al. | |
| 2010/0204602 A1 | 8/2010 | Addington et al. | |
| 2010/0250280 A1 * | 9/2010 | Sutherland ........ | A61M 15/0065 705/3 |
| 2010/0294278 A1 | 11/2010 | Mosier et al. | |
| 2010/0326438 A1 | 12/2010 | Dunne | |
| 2011/0030706 A1 | 2/2011 | Gibson et al. | |
| 2011/0036346 A1 | 2/2011 | Cohen et al. | |
| 2011/0038958 A1 | 2/2011 | Kikuchi et al. | |
| 2011/0126831 A1 | 6/2011 | Fernandez Pernia | |
| 2011/0244020 A1 | 10/2011 | Hale et al. | |
| 2011/0265806 A1 | 11/2011 | Alarcon et al. | |
| 2012/0252885 A1 | 10/2012 | Barbato | |
| 2012/0255546 A1 | 10/2012 | Goetz et al. | |
| 2012/0304990 A1 * | 12/2012 | Todd .................... | A61M 11/042 128/203.14 |
| 2012/0325227 A1 | 12/2012 | Robinson et al. | |
| 2013/0032139 A1 | 2/2013 | Hale et al. | |
| 2013/0081623 A1 | 4/2013 | Buchberger | |
| 2013/0087144 A1 | 4/2013 | Todd | |
| 2013/0112197 A1 | 5/2013 | Kruener et al. | |
| 2013/0213397 A1 * | 8/2013 | Curtis ............... | A61M 15/0045 128/203.15 |
| 2013/0276799 A1 | 10/2013 | Davidson et al. | |
| 2013/0333700 A1 | 12/2013 | Buchberger | |
| 2014/0060525 A1 | 3/2014 | Hale et al. | |
| 2014/0088045 A1 | 3/2014 | Rigas et al. | |
| 2014/0100249 A1 | 4/2014 | Sears et al. | |
| 2014/0144429 A1 | 5/2014 | Wensley et al. | |
| 2014/0190496 A1 | 7/2014 | Wensley et al. | |
| 2014/0238423 A1 | 8/2014 | Tucker et al. | |
| 2015/0064672 A1 | 3/2015 | Bars | |
| 2015/0075521 A1 | 3/2015 | Lee et al. | |
| 2015/0090253 A1 | 4/2015 | Farrow | |
| 2015/0122252 A1 | 5/2015 | Frija | |
| 2015/0136124 A1 | 5/2015 | Aronie et al. | |
| 2015/0237913 A1 | 8/2015 | Suzuki et al. | |
| 2016/0007653 A1 | 1/2016 | Tu | |
| 2016/0044960 A1 | 2/2016 | O'Connor | |
| 2016/0100624 A1 | 4/2016 | Yilmaz et al. | |
| 2016/0166786 A1 | 6/2016 | Kinzer | |
| 2016/0171164 A1 | 6/2016 | Kinzer | |
| 2016/0183589 A1 | 6/2016 | Born et al. | |
| 2016/0271347 A1 | 9/2016 | Raichman | |
| 2016/0286860 A1 | 10/2016 | Flayler | |
| 2016/0295922 A1 | 10/2016 | John et al. | |
| 2016/0331022 A1 | 11/2016 | Cameron | |

(56) References Cited

U.S. PATENT DOCUMENTS

| | | |
|---|---|---|
| 2016/0331913 A1 | 11/2016 | Bourque |
| 2017/0095624 A1 | 4/2017 | Davidson et al. |
| 2017/0106153 A1 | 4/2017 | Davidson et al. |
| 2017/0119979 A1 | 5/2017 | Davidson et al. |
| 2017/0119981 A1 | 5/2017 | Davidson et al. |
| 2017/0127727 A1 | 5/2017 | Davidson et al. |
| 2017/0136196 A1 | 5/2017 | Davidson et al. |
| 2017/0150755 A1 | 6/2017 | Batista |
| 2017/0157343 A1 | 6/2017 | Davidson et al. |
| 2017/0164657 A1 | 6/2017 | Batista |
| 2017/0360089 A1 | 12/2017 | Davidson et al. |

FOREIGN PATENT DOCUMENTS

| | | |
|---|---|---|
| GB | 2108390 | 5/1983 |
| GB | 2340758 | 3/2000 |
| GB | 2495771 | 4/2013 |
| WO | WO 98/04308 | 2/1998 |
| WO | WO 00/24362 | 5/2000 |
| WO | WO 03/037412 | 5/2003 |
| WO | WO 2005/061033 | 7/2005 |
| WO | WO 2008/024408 | 2/2008 |
| WO | WO 2008/024490 | 2/2008 |
| WO | WO 2008/116165 | 9/2008 |
| WO | WO 2009/124552 | 10/2009 |
| WO | WO 2010/015260 | 2/2010 |
| WO | WO 2011/073306 | 6/2011 |
| WO | WO 2012/006125 | 1/2012 |
| WO | WO 2012/006126 | 1/2012 |
| WO | WO 2012/026963 | 3/2012 |
| WO | WO 2012/085919 | 6/2012 |
| WO | WO 2013/057185 | 4/2013 |
| WO | WO 2013/083636 | 6/2013 |
| WO | WO 2014061477 | 4/2014 |
| WO | WO 2015/123064 | 8/2015 |
| WO | WO 2015/123317 | 8/2015 |
| WO | WO 2015/175979 | 11/2015 |
| WO | WO 2016/001921 | 1/2016 |
| WO | WO 2016/001922 | 1/2016 |
| WO | WO 2016/001923 | 1/2016 |
| WO | WO 2016/001924 | 1/2016 |
| WO | WO 2016/001925 | 1/2016 |
| WO | WO 2016/001926 | 1/2016 |
| WO | WO 2016/090303 | 6/2016 |
| WO | WO 2016/147188 | 9/2016 |
| WO | WO 2016/172802 | 11/2016 |
| WO | WO 2016/187696 | 12/2016 |
| WO | WO 2017/118980 | 7/2017 |

OTHER PUBLICATIONS

Official Action dated Apr. 10, 2017 From the US Patent and Trademark Office Re. U.S. Appl. No. 15/362,883. (33 pages).

Official Action dated Mar. 9, 2017 From the US Patent and Trademark Office Re. U.S. Appl. No. 15/386,182. (24 pages).

Official Action dated Mar. 13, 2017 From the US Patent and Trademark Office Re. U.S. Appl. No. 15/391,896. (22 pages).

International Preliminary Report on Patentability dated Jan. 12, 2017 From the International Bureau of WIPO Re. Application No. PCT/IL2015/050673. (15 Pages).

International Preliminary Report on Patentability dated Jan. 12, 2017 From the International Bureaw of WIPO Re. Application No. PCT/IL2015/50676. (11 Pages).

Communication Relating to the Results of the Partial International Search dated Oct. 22, 2015 From the International Searching Authority Re. Application No. PCT/IL2015/050673.

Communication Relating to the Results of the Partial International Search dated Sep. 24, 2015 From the International Searching Authority Re. Application No. PCT/IL2015/050677.

International Search Report and the Written Opinion dated Feb. 2, 2016 From the International Searching Authority Re. Application No. PCT/IL2015/050673.

International Search Report and the Written Opinion dated Dec. 3, 2015 From the International Searching Authority Re. Application No. PCT/IL2015/050677.

International Search Report and the Written Opinion dated Jan. 7, 2016 From the International Searching Authority Re. Application No. PCT/IL2015/050675.

International Search Report and the Written Opinion dated Dec. 10, 2015 From the International Searching Authority Re. Application No. PCT/IL2015/050674.

International Search Report and the Written Opinion dated Jan. 20, 2016 From the International Searching Authority Re. Application No. PCT/IL2015/50676.

International Search Report and the Written Opinion dated Oct. 22, 2015 From the International Searching Authority Re. Application No. PCT/IL2015/050678.

AAAAI "Inhaled Asthma Medications: Tips to Remember", American Academy of Allergy Asthma & Immunology, AAAAI, 4 P., 2013.

Abrams et al. "Vaporization as a Smokeless Cannabis Delivery System: A Pilot Study", Clinical Pharmacology & Therapeutics, 82(5): 572-578, Advance Online Publication Apr. 11, 2007.

Bhattacharyya et al. "Opposite Effects of Delta-9-Tetrahydrocannabinol and Cannabidiol on Human Brain Function and Psychopathology", Neuropsychopharmacology, 35: 764-774, 2010.

Boden et al. "The Effects of Cannabis Use Expectancies on Self-Initiated Cannabis Cessation", Addiction, 108: 1649-1657, 2013.

Das et al. "Effects of 9-Ene-Tetrahydrocannabinol on Expression of Beta-Type Transforming Growth Factors, Insulin-Like Growth Factor-I and C-Myc Genes in the Mouse Uterus", The Journal of Steroid Biochemistry and Molecular Biology, 45(6): 459-465, 1993.

Eisenberg et al. "The Pharmacokinetics, Efficacy, Safety, and Ease of Use of a Novel Portable Metered-Dose Cannabis Inhaler in Patients With Chronic Neuropathic Pain: A Phase 1a Study", Journal of Pain & Palliative Care Pharmacotherapy, 28(3): 216-225, Published Online Aug. 13, 2014.

Farrimond et al. "Cannabinol and Cannabidiol Exert Opposing Effects on Rat Feeding Patterns", Psychopharmacology, 223: 117-129, 2012.

FDA "Guidance for Industry. Population Pharmacokinetics", U.S. Department of Health and Human Services, Food and Drug Administration (FDA), Center for Drug Evaluation and Research (CDER), Center for Biological Evaluation and Research (CBER), CP 1: 1-31, Feb. 1999.

Hazekamp et al. "Bedrocan®—Stimulating the Development of Herbal Cannabis-Based Products", Bedromedical Presentation, 2013.

Hazekamp et al. "Evaluation of a Vaporizing (Volcano®) for the Pulmonary Administration of Tetrahydrocannabinol", Journal of Pharmaceutical Sciences, 95(6): 1308-1317, Jun. 2006.

Hazekamp et al. "The Medicinal Use of Cannabis and Cannabinoids—An International Cross-Sectional Survey on Administration Forms", Journal of Psychoactive Drugs, 45(3): 199-210, 2013.

Herbalizer "Herbalizer, the New Vaporization Experience", 6 P., Jun. 7, 2013.

Jamontt et al. "The Effects of Delta[9]-Tetrahydrocannabinol and Cannabidiol Alone and in Combination on Damage, Inflammation and In Vitro Motility Disturbances in Rat Colitis", British Journal of Pharmacology, 160: 712-723, 2010.

McPartland et al. "Are Cannabidiol and Delta9-Tetrahydrocannabivarin Negative Modulators of the Endocannabinoid System? A Systematic Review", British Journal of Pharmacology, 172(3): 737-753, Published Online Jan. 8, 2015.

Mechoulam et al. "Cannabidiol—Recent Advances", Chemistry & Biodiversity, 4: 1678-1692, 2007.

Pertwee "The Diverse CB1 and CB2 Receptor Pharmacology of Three Plant Cannabinoids: Delta[9]-Tetrahydrocannabinol, Cannabidiol and Delta[9]-Tetrahydrocannabivarin", British Journal of Pharmacology, 153: 199-215, 2008.

Rabinowitz et al. "Fast Onset Medications Through Thermally Generated Aerosols", The Journal of Pharmacological and Experimental Therapeutics, 309(2): 769-775, 2004.

(56) References Cited

OTHER PUBLICATIONS

Rau "The Inhalation of Drugs: Advantages and Problems", Respiratory Care, 50(3): 367-382, Mar. 2005.
Strougo et al. "Modelling of the Concentration—Effect Relationship of THC on Central Nervous System Parameters and Heart Rate—Insight Into Its Mechanisms of Action and a Tool for Clinical Research and Development of Cannabinoids", Journal of Pharmacology, 22(7): 717-726, Sep. 2008.
Syqe Medical "The World's First Metered Dose Pharmaceutical Grade Medical Cannabis Inhaler", Syqe Medical™, Press Kit, p. 1-8, 2015.
Van Gerven "Biomarkers to Assess Adverse Drug Effects on the CNS", Centre for Human Drug Research, CHDR, Poster-Session, Slide-Show, 25 P., 2013.
Van Hell et al. "Evidence for Involvement of the Insula in the Psychotropic Effects of THC in Humans: A Double-Blind, Randomized Pharamcological MRI Study", International Journal of Neuropharmacology, 14: 1377-1388, 2011.
Vann et al. "Divergent Effects of Cannabidiol on the Discriminative Stimulus and Place Conditioning Effects of Delta 9-Tetrahydrocannabiol", Drug and Alcohol Dependence, 94(1-3): 191-198, Apr. 1, 2008.
Vemuri et al. "Pharmacotherapeutic Targeting of the Endocannabinoid Signaling System: Drugs for Obesity and the Metabolic Syndrome", Physiology & Behavior, 93: 671-686, 2008.
Wallace et al. "Efficacy of Inhaled Cannabis on Painful Diabetic Neuropathy", The Journal of Pain, 169(7): 616-627, Published Online Apr. 3, 2015.
Ware et al. "Smoked Cannabis for Chronic Neuropathic Pain: A Randomized Controlled Trial", Canadian Medical Association Journal, CMAJ, 182(14): E694-E701, Published Online Aug. 30, 2010.
Wilsey et al. "Low-Dose Vaporized Cannabis Significantly Improves Neuropathic Pain", The Journal of Pain, 14(2): 136-148, Published Online Dec. 13, 2012.
Zuurman et al. "Biomarkers for the Effects of Cannabis and THC in Healthy Volunteers", British Journal of Clinical Pharmacology, 67(1): 5-21, 2008.
Zuurman et al. "Effect of Intrapulmonary Tetrahydrocannabinol Administration in Humans", Journal of Psychopharmacology, 22(7): 707-716, 2008.
Notice of Allowance dated Jun. 1, 2017 From the US Patent and Trademark Office Re. U.S. Appl. No. 13/997,302. (24 Pages).
Official Action dated Jun. 1, 2017 From the US Patent and Trademark Office Re. U.S. Appl. No. 15/375,098. (42 pages).
Jang et al. "Thermophysical Properties of Porous SiC Ceramics Fabricated by Pressureless Sintering", Science and Technology of Advanced Materials, 8(7): 655-659, Nov. 30, 2007.
Norwood et al. "Best Practices for Extractables and Leachables in Orally Inhaled and Nasal Drug Products: An Overview of the PQRI Recommendations", Pharmaceutical Research, 25(4): 727-739, Published Online Jan. 9, 2008.
Applicant-Initiated Interview Summary dated May 22, 2017 From the US Patent and Trademark Office Re. U.S. Appl. No. 15/386,182. (3 pages).
Applicant-Initiated Interview Summary dated May 23, 2017 From the US Patent and Trademark Office Re. U.S. Appl. No. 15/362,841. (3 pages).
Applicant-Initiated Interview Summary dated May 23, 2017 From the US Patent and Trademark Office Re. U.S. Appl. No. 15/362,883. (3pages).
Applicant-Initiated Interview Summary dated May 23, 2017 From the US Patent and Trademark Office Re. U.S. Appl. No. 15/375,098. (3 pages).
Applicant-Initiated Interview Summary dated May 23, 2017 From the US Patent and Trademark Office Re. U.S. Appl. No. 15/382,819. (3 pages).
International Search Report and the Written Opinion dated Mar. 27, 2017 From the International Searching Authority Re. Application No. PCT/IL2017/050014. (16 Pages).
Official Action dated Apr. 6, 2017 From the US Patent and Trademark Office Re. U.S. Appl. No. 15/362,841. (35 pages).
Official Action dated Aug. 18, 2017 From the US Patent and Trademark Office Re. U.S. Appl. No. 15/308,370. (56 pages).
Communication Pursuant to Article 94(3) EPC dated Jun. 23, 2017 From the European Patent Office Re. Application No. 11815728.8. (5 Pages)
Ibrahim et al. "Inhalation Drug Delivery Devices: Technology Update", Medical Devices: Evidence and Research, 8: 131-139, Feb. 12, 2015.
Lanz et al. "Medicinal Cannabis: In Vitro Validation of Vaporizers for the Smoke-Free Inhalation of Cannabis", Plos One, 11(1): e0147286-1-e0147286-18, Jan. 19, 2016.
Pomahacova et al. "Cannabis Smoke Condensate III: The Cannabinoid Content of Vaporised Cannabis Sativa", Inhalation Toxicology, 21(13): 1108-1112, Nov. 1, 2009.
Communication Relating to the Results of the Partial International Search dated May 18, 2012 From the International Searching Authority Re. Application No. PCT/IL2011/050071.
International Preliminary Report on Patentability dated Jul. 2, 2013 From the International Preliminary Examining Authority Re. Application No. PCT/IL2011/050071.
International Preliminary Report on Patentability dated Jan. 12, 2017 From the International Bureau of WIPO Re. Application No. PCT/IL2015/050674. (11 Pages).
International Preliminary Report on Patentability dated Jan. 12, 2017 From the International Bureau of WIPO Re. Application No. PCT/IL2015/050675. (8 Pages).
International Preliminary Report on Patentability dated Jan. 12, 2017 From the International Bureau of WIPO Re. Application No. PCT/IL2015/050677. (13 Pages).
International Preliminary Report on Patentability dated Jan. 12, 2017 From the International Bureau of WIPO Re. Application No. PCT/IL2015/050678. (12 Pages).
International Search Report and the Written Opinion dated Oct. 19, 2012 From the International Searching Authority Re. Application No. PCT/IL2011/050071.
Office Action dated Jan. 19, 2017 From the Israel Patent Office Re. Application No. 227102 and Its Translation Into English. (5 Pages).
Office Action dated Jun. 22, 2016 From the Israel Patent Office Re. Application No. 227102 and Its Translation Into English.
Official Action dated Jan. 30, 2017 From the US Patent and Trademark Office Re. U.S. Appl. No. 13/997,302. (23 pages).
Official Action dated Sep. 30, 2016 From the US Patent and Trademark Office Re. U.S. Appl. No. 13/997,302.
Restriction Official Action dated Jul. 8, 2016 From the US Patent and Trademark Office Re. U.S. Appl. No. 13/997,302.
Written Opinion dated Apr. 22, 2013 From the International Preliminary Examining Authority Re. Application No. PCT/IL2011/050071.
Applicant-Initiated Interview Summary dated Dec. 22, 2017 From the US Patent and Trademark Office Re. U.S. Appl. No. 15/362,883. (3 pages).
Official Action dated Dec. 26, 2017 From the US Patent and Trademark Office Re. U.S. Appl. No. 15/391,896. (53 pages).
Official Action dated Nov. 1, 2017 From the US Patent and Trademark Office Re. U.S. Appl. No. 15/382,819. (45 pages).
Applicant-Initiated Interview Summary dated Jan. 5, 2018 From the US Patent and Trademark Office Re. U.S. Appl. No. 15/382,819. (3 pages).
Requisition by the Examiner dated Nov. 16, 2017 From the Innovation, Science and Economic Development Canada, Canadian Intellectual Property Office Re. Application No. 2,822,738. (4 Pages).
Office Action dated Dec. 21, 2017 From the Israel Patent Office Re. Application No. 227102 and Its Translation Into English. (4 Pages).
Official Action dated Dec. 12, 2017 From the US Patent and Trademark Office Re. U.S. Appl. No. 15/308,370. (27 pages).
Official Action dated Jan. 25, 2018 From the US Patent and Trademark Office Re. U.S. Appl. No. 15/375,098. (37 pages).
Examiner-Initiated Interview Summary dated Nov. 2, 2017 From the US Patent and Trademark Office Re. U.S. Appl. No. 15/382,819. (2 pages).

(56) References Cited

OTHER PUBLICATIONS

Official Action dated Sep. 22, 2017 From the US Patent and Trademark Office Re. U.S. Appl. No. 15/362,883. (43 pages).
Communication Pursuant to Article 94(3) EPC dated Jan. 22, 2018 From the European Patent Office Re. Application No. 15756490.7. (4 Pages).
Assaf et al. "Pre- and Post-Conditioning Treatment With an Ultra-Low Dose of [Delta]sup9-Tetrahydrocannabinol (THC) Protects Against Pentylenetetrazole (PTZ)-Induced Cognitive Damage", Behavioral Brain Research, 220(1): 194-201, Jun. 2011.
Fishbein et al. "Long-Term Behavioral and Biochemical Effects of an Ultra-Low Dose of [Delta]sup9-Tetrahydrocannabinol (THC): Neuroprotection and ERK Signaling", Experimental Brain Research, 221(4): 437-448, Published Online Jul. 22, 2012.
Communication Pursuant to Article 94(3) EPC dated Jan. 19, 2018 From the European Patent Office Re. Application No. 15744363.1. (4 Pages).

\* cited by examiner

FLOW REGULATING INHALER DEVICE

RELATED APPLICATIONS

This application is a National Phase of PCT Patent Application No. PCT/IL2015/050678 having International filing date of Jun. 30, 2015, which claims the benefit of priority under 35 USC § 119(e) of U.S. Provisional Patent Application No. 62/085,772 filed on Dec. 1, 2014; U.S. Provisional Patent Application No. 62/035,588 filed on Aug. 11, 2014; U.S. Provisional Patent Application No. 62/086,208 filed on Dec. 2, 2014; U.S. Provisional Patent Application No. 62/164,710 filed on May 21, 2015; and U.S. Provisional Patent Application No. 62/019,225 filed on Jun. 30, 2014; the contents of which are incorporated herein by reference in their entirety.

PCT Patent Application No. PCT/IL2015/050678 was co-filed with PCT Patent Application Nos. PCT/IL2015/050673 entitled METHOD AND DEVICE FOR VAPORIZATION AND INHALATION OF ISOLATED SUBSTANCES, PCT/IL2015/050677 entitled DRUG DOSE CARTRIDGE FOR AN INHALER DEVICE, and PCT/IL2015/050676, PCT/IL2015/050674, PCT/IL2015/050675 entitled METHODS, DEVICES AND SYSTEMS FOR PULMONARY DELIVERY OF ACTIVE AGENTS, the contents of which are incorporated herein by reference in their entirety.

FIELD AND BACKGROUND OF THE INVENTION

The present disclosure, in some embodiments thereof, relates to pulmonary delivery of a substance using a personal inhaler device and, more particularly, but not exclusively, to controlling flow through an inhaler.

U.S. Pat. No. 5,655,520 teaches "A nebulizer is improved by placing a flexible valve in the ambient air inlet tube. Inhalation suction and Venturi effect shut down the flexible valve in proportion to the strength of the inhalation. Thus, the same output flow rate is obtained even with variable strength inhalations. Medications can be properly administered by controlled inhalation flow rates. In an alternate embodiment a metered dose inhaler (MDI) is outfitted with a similar flexible valve. Once again the patient is forced to inhale at a constant flow rate, thus causing the medication to seep deeply into the lungs. In both embodiments the flexible valve is preferably shaped in a duck billed fashion with air flow flowing toward the narrow end of the duck bill."

SUMMARY OF THE INVENTION

According to an aspect of some embodiments, there is provided an inhaler device for delivery to an inhaling user of at least one drug substance emitted from a dose cartridge, the inhaler device comprising: a first conduit for conducting a carrier airflow to a proximal opening of a mouthpiece from which the user inhales; a holder configured to position the dose cartridge at a dose cartridge position defined by the holder within the carrier airflow of the first conduit; a second conduit, pneumatically coupled to the first conduit, for conducting a shunting airflow to the mouthpiece without passing the shunting airflow through the dose cartridge position; and at least one valve in at least one of the first and second conduits; wherein the at least one valve is operated by a valve controller to control a rate of carrier airflow in response to a negative pressure generated by the inhaling user.

According to some embodiments, the inhaler device comprises at least one sensor positioned and configured for detecting at least one parameter indicating a rate of the carrier airflow.

According to some embodiments, the at least one sensor comprises a pressure sensor positioned in the first conduit proximal to the dose cartridge position.

According to some embodiments, the valve controller is functionally connected to receive an indication of the rate of the carrier airflow from the at least one sensor, and to operate the at least one valve based on the indication of the rate of the carrier airflow and a target profile for the carrier airflow.

According to some embodiments, the indicating parameter comprises a rate of the carrier airflow sensed while the second conduit is at least partially obstructed.

According to some embodiments, the valve controller is configured to operate the at least one valve based on a difference between the target profile and the rate of the carrier airflow sensed while the second conduit is at least partially obstructed.

According to some embodiments, the controller is configured to modify the target profile based on the received indication of the rate of carrier airflow.

According to some embodiments, the second conduit is connected to at least the first conduit at a junction between the dose cartridge position and the proximal opening of the mouthpiece, and the junction is configured to conduct airflow from the second conduit to circumferentially surround the carrier airflow.

According to some embodiments, the valve controller is configured to substantially reduce a total rate of airflow to the user for an intermediate period after a first period of airflow.

According to some embodiments, the substantial reduction in the rate of total airflow is to no more than 50% of the total rate of airflow during the first period of airflow.

According to some embodiments, the bypass airflow through the third conduit is controlled by a bypass valve.

According to some embodiments, the third conduit comprises a plurality of tracts.

According to some embodiments, the inhaler device comprises a bypass valve controller functionally connected to operate the bypass valve to control airflow through the third conduit.

According to some embodiments, the valve controller and/or bypass valve controller are configured to substantially reduce a total rate of airflow to the user for an intermediate period after a first period of airflow, and then open at least the third conduit.

According to some embodiments, a summed cross-sectional area of the proximal openings of the first and third conduits is at least 25% larger than the proximal opening of the first conduit.

According to some embodiments, a minimal cross section through which the flow passes to the user along the third conduit is at least 25% larger than a minimal cross section through which the flow passes to the user through the first conduit.

According to some embodiments, the at least one valve and at least one bypass valve comprise a plurality of valve apertures arranged on a mounting movable at least from a first position to a second position, such that moving to the second position aligns a valve aperture to close of one of the conduits, while also aligning a valve aperture to at least partially open another of the conduits.

According to some embodiments, the mounting comprises at least one rotating disc having at least one valve aperture passing therethrough, and the rotating disc is rotatable at least from the first position to the second position to change the alignment of the aperture to the conduit.

According to some embodiments, the mounting comprises: at least one inner tube having apertures into the conduits; and at least one outer tube having a wall surrounding the inner tube and having the at least one valve aperture through the wall of the at least one outer tube; wherein the at least one outer tube and the at least one inner tube are movable with respect to the other at least from the first position to the second position to change the alignment of the apertures to the conduits.

According to some embodiments, the at least one outer tube comprises two separately movable outer tubes; and wherein moving one of the two separately movable outer tubes controls the degree of opening of one conduit, and moving the other controls the degree of opening of another conduit.

According to some embodiments, the inhaler device comprises a heating assembly configured to heat material of the drug dose cartridge comprising the at least one drug substance to vaporize the at least one drug substance from the material, wherein the released vapors flow into the first conduit and enter the carrier airflow.

According to some embodiments, the heating assembly comprises an electrode configured to apply an electric current to an electrically resistive heating element of the dose cartridge, when the dose cartridge is positioned by the holder.

According to some embodiments, the inhaler device comprises: at least one sensor positioned and configured for detecting at least one parameter indicating a rate of the carrier airflow; and a heating controller functionally connected to control heating of the material of the drug dose cartridge, based on the at least one parameter indicating the rate of carrier airflow.

According to some embodiments, the heating controller is configured to stop heating if the rate of carrier airflow drops below a threshold.

According to some embodiments, the heating controller is functionally connected to receive an indication of the temperature from the temperature sensor, and to operate the at least one valve based on the indication of the temperature.

According to some embodiments, the valve controller operates the at least one valve to reduce the carrier airflow if the temperature falls below a threshold.

According to some embodiments, the target profile comprises a constant flow rate through the first conduit and the dose cartridge position for at least a certain period.

According to some embodiments, the heating controller is configured to activate drug substance release when commencement of inhalation by the user is detected or when the rate of carrier airflow is above a threshold.

According to some embodiments, at least the valve controller is configured to communicate with one or more of a user interface and a physician interface.

According to some embodiments, the at least one valve is operable by the valve controller based on one or more of: a flow rate of inhalation, a flow rate through the dose cartridge position, and a defined time from a detected or estimated event.

According to some embodiments, the inhaler device comprises a fan positioned to affect carrier airflow through the first conduit.

According to some embodiments, a fan controller is functionally connected to operate the fan to induce airflow based on the indication of the rate of carrier airflow from the sensor and a target profile for the carrier airflow.

According to some embodiments, the at least one valve comprises a valve positioned along the first conduit.

According to some embodiments, the at least one valve comprises a valve positioned along the second conduit configured to at least partially close to limit a rate of shunting airflow, and thereby to affect the rate of carrier airflow.

According to some embodiments, the valve controller comprises a portion of the at least one valve mechanically configured to adjust a degree of opening of the at least one valve based on at least one of the shunting airflow and the carrier airflow.

According to some embodiments, the holder positions the dose cartridge such that at least 90% of the carrier airflow through the first conduit passes through the dose cartridge.

According to some embodiments, the second conduit is connected to the first conduit at a junction located between the dose cartridge position and the proximal opening of the mouthpiece.

According to some embodiments, at least one of the first and second conduits comprises a plurality of airflow tracts.

According to an aspect of some embodiments, there is provided an inhaler device for delivery to an inhaling user of at least one drug substance emitted from a dose cartridge, the inhaler device comprising: an at least first conduit for conducting at least a carrier airflow to a proximal opening of a mouthpiece from which the user inhales; a holder configured to position the dose cartridge at a dose cartridge position defined by the holder within the carrier airflow of the at least first conduit; a bypass conduit configured to conduct a bypass airflow to the proximal opening of the mouthpiece through a path separated from the at least first conduit; and a controller configured for controlling at least the bypass airflow during a single inhalation such that the rate of total airflow to the proximal opening of the mouthpiece in a first inhalation period is significantly less than a rate of total airflow to the proximal opening of the mouthpiece in a later inhalation period.

According to some embodiments, the rate of total airflow in the later inhalation period is at least 100% larger than during the first inhalation period.

According to some embodiments, the controller is configured to control flow through the device during a period intermediate to the first inhalation period and the later inhalation period such that a total rate of airflow to the proximal opening of the mouthpiece during the intermediate period is significantly lower than in the first inhalation period.

According to some embodiments, the rate of total airflow in the first inhalation period is at least 100% larger than during the intermediate inhalation period.

According to some embodiments, the bypass conduit is connected to the first conduit at a junction between the dose cartridge position and the proximal opening of the mouthpiece, and the junction is configured to conduct the bypass airflow to circumferentially surround the carrier airflow.

According to an aspect of some embodiments, there is provided an inhaler device for delivery to an inhaling user of at least one drug substance emitted from a dose cartridge, the inhaler device comprising: an at least first conduit for conducting at least a carrier airflow to a proximal opening of a mouthpiece from which the user inhales; a holder configured to position the dose cartridge at a dose cartridge position defined by the holder within the carrier airflow of the at least first conduit; a bypass conduit configured to conduct a bypass airflow to the proximal opening of the mouthpiece through a path separated from the at least first conduit; and a controller configured for controlling at least the bypass airflow and the carrier airflow during a single inhalation such that the rate of total airflow to the proximal opening of the mouthpiece in an intermediate inhalation period is significantly less than a rate of total airflow to the proximal opening of the mouthpiece during both a later and an earlier inhalation period.

According to an aspect of some embodiments, there is provided a method of pulmonary delivery of at least one drug substance from a heated drug dose to a user inhaling from an inhaler device, the method comprising: estimating a rate of release of the drug substance from the heated drug dose to an inhalation-induced carrier airflow passing the drug dose cartridge; controlling at least one of the heating of the drug dose and the rate of carrier airflow such that the drug substance release matches a target profile of drug substance release.

According to some embodiments, estimating the rate of release comprises estimating a rate of carrier airflow through the drug dose cartridge.

According to some embodiments, the rate of carrier airflow is adjusted by dynamically controlling an inhalation-induced shunting airflow which bypasses the drug dose cartridge.

According to some embodiments, the shunting airflow is conducted to circumferentially surround the carrier airflow, such that airflow comprising a relatively high drug substance concentration is surrounded by airflow comprising a lower drug substance concentration.

According to some embodiments, the method comprises estimating a total inhalation rate by limiting airflow in the device to carrier airflow, such that the estimated rate of carrier airflow is equivalent to a total inhalation flow rate, and controlling to match the target profile of drug substance release based on the estimated total inhalation flow rate.

According to some embodiments, a heating pattern applied to the drug dose is adjusted to match a target profile of drug substance release.

According to some embodiments, adjustment of the heating pattern includes controlling at least one of a rate of heating, a frequency of applying heating, a target temperature and a period of time in which one or more given temperatures are maintained.

According to some embodiments, a target profile of drug substance release is at least partially specified by heating of the drug dose as a function of the rate of carrier airflow.

According to some embodiments, a target profile of drug substance release is at least partially specified by the rate of carrier airflow as a function of the heating of the drug dose.

According to some embodiments, the controlling comprises modifying a pressure differential across the drug dose cartridge.

According to some embodiments, the controlling comprises adjusting the opening of one or more valves.

According to some embodiments, the target profile of drug substance release is at least partially specified in terms of a rate of carrier airflow.

According to some embodiments, the specified rate of carrier airflow comprises a constant rate of carrier airflow for a certain period.

According to some embodiments, the target profile of drug substance release is at least partially specified in terms of the heating of the drug dose.

According to some embodiments, the specified heating of the drug dose comprises maintaining a drug dose temperature for a certain period.

According to some embodiments, the method comprises modifying the target profile during while the user is inhaling.

According to some embodiments, the heated drug dose comprises a botanical substance, and the heating is applied to vaporize the at least one drug substance.

According to some embodiments, the botanical substance comprises *cannabis*, and the at least one drug substance comprises THC.

According to some embodiments, the method comprises flushing drug dose residues from at least one of a conduit of the inhaler device and a dose cartridge by allowing only carrier airflow through the device.

According to some embodiments, the method comprises flushing drug dose residues by allowing only carrier airflow for a period after heating of the material is stopped.

According to an aspect of some embodiments, there is provided an inhaler device for providing to an inhaling user a flow-based status indication, the inhaler device comprising: at least one conduit for conducting airflow to a mouthpiece from which the user inhales; at least one valve operable to modulate resistance to the airflow conducted through the conduit; and a controller functionally connected to the control the valve to generate a pattern of airflow modulations indicating a status of the inhaler device to the user.

According to some embodiments, the pattern of airflow modulations indicates successful operation of the inhaler.

According to an aspect of some embodiments, there is provided a method of manipulating flow through an inhaler device to provide a respiration-based indication to a user inhaling through the inhaler device, comprising: allowing a first period of airflow through the inhaler device during an inhalation; at least partially obstructing the airflow so that a reduction in flow is sensed by the user; allowing a second period of less obstructed airflow through the inhaler device during a continuation of the same inhalation.

According to some embodiments, airflow during the first period carries a drug substance from the inhaler to the pulmonary system of the user, and wherein airflow during the second period advances a drug substance inhaled during the first period deeper within the pulmonary system.

According to some embodiments, a rate of airflow during the first period is controlled based on a target profile of flow through a drug dose cartridge carrying the drug substance and held within the inhaler device.

According to some embodiments, the releasing is ceased before the obstructing.

According to some embodiments, a rate of airflow during the second period is at least 50% greater than during the first period.

According to some embodiments, a sequence of flow manipulations indicates to the user that a use session is completed.

According to some embodiments, the device is configured to provide the user with an additional audio, visual and/or tactile indication that a use session is completed.

According to some embodiments, at least one of the allowing a first period of airflow, obstructing the airflow and allowing a second period of less obstructed airflow is performed such that a total volume of flow reaching the user during the second period is larger than a volume of an anatomical dead space of the user.

According to some embodiments, the period of obstructing is selected according to a sensed parameter of the airflow during the first period.

According to some embodiments, the sensed parameter comprises a rate of airflow.

According to some embodiments, the period of obstructing is extended when a low inhalation flow rate is sensed during the first period.

According to some embodiments, the length of the period of obstructing is based on allowing inhalation effort measured during the first period to continue long enough that a negative pressure develops causing a calculated minimum volume to be inhaled once airflow resumes in the second period.

According to some embodiments, the degree of obstructing is selected according to a sensed parameter of the pressure during the obstruction period.

According to some embodiments, the at least partial obstructing of the airflow is increased when a sensed parameter of the pressure during the obstruction period indicates an inhalation force below a threshold.

According to some embodiments, the at least partially obstructing the airflow is performed for a period of between 5 and 400 msec.

According to an aspect of some embodiments, there is provided a inhaler device comprising: at least one inner tube comprising a wall having at least one aperture in pneumatic communication with a central conduit extending longitudinally within the inner tube; and at least one outer tube having a wall surrounding at least a portion of the at least one inner tube and having at least one aperture through the wall of the at least one outer tube; wherein the at least one outer tube and the at least one inner tube are movable with respect to each other at least from a first position to a second position to change the alignment of the apertures in the inner and outer tubes, such that moving to the second position moves an outer tube aperture away from alignment with an inner tube aperture to reduce an opening leading to the central conduit, while also aligning an outer tube aperture with an inner tube aperture to increase an opening leading to the central conduit.

According to some embodiments, the inhaler device comprises a plurality of holders.

According to some embodiments, the first conduit comprises a plurality of drug conduit tracts, and the plurality of holders comprises holders located in corresponding drug conduit tracts.

According to some embodiments, the plurality of holders comprises at least two holders located in a common drug conduit tract.

According to some embodiments, the holder positions the dose cartridge within the first conduit such that such that the electrode of the heating assembly is sealed from the carrier airflow.

According to some embodiments, the holder positions the dose cartridge such that substantially all of the carrier airflow through the first conduit passes through the dose cartridge.

According to an aspect of some embodiments, there is provided an inhaler device for delivery to an inhaling user of at least one drug substance emitted from a dose cartridge, the inhaler device comprising: a holder configured to position the dose cartridge at a dose cartridge position defined by the holder, the defined position being such that the least one drug substance emitted from the dose cartridge enters a carrier airflow; a first conduit for conducting the carrier airflow from the dose cartridge position to a proximal opening of a mouthpiece from which the user inhales; a second conduit, pneumatically coupled to the first conduit, for conducting a shunting airflow to the mouthpiece without passing the shunting airflow through the dose cartridge position; and at least one valve in at least one of the first and second conduits; wherein the at least one valve is operated by a valve controller to control a rate of carrier airflow in response to a negative pressure generated by the inhaling user.

According to an aspect of some embodiments, there is provided an inhaler device for delivery to an inhaling user of at least one drug substance emitted from a dose cartridge, the inhaler device comprising: a holder configured to position the dose cartridge at a dose cartridge position defined by the holder, the defined position being such that the least one drug substance emitted from the dose cartridge enters a carrier airflow; a first conduit for conducting the carrier airflow from the dose cartridge position to a proximal opening of a mouthpiece from which the user inhales; and a second conduit, connected to the first conduit at a junction between the dose cartridge position and the proximal opening of the mouthpiece, for conducting a shunting airflow to the mouthpiece without passing the shunting airflow through the dose cartridge position; wherein the junction is configured to conduct airflow from the second conduit to circumferentially surround the carrier airflow.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, examples for methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. One or more tasks according to some embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
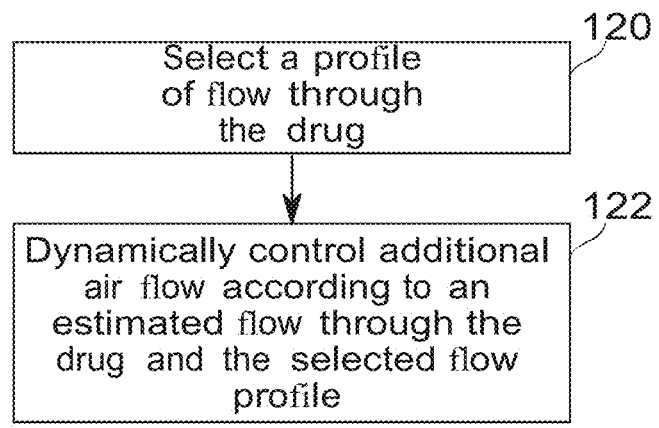
FIGS. 1A-1B are schematic flowcharts of general (FIG. 1A) and detailed (FIG. 1B) methods for pulmonary delivery of one or more drug substances to a user using an inhaler device, according to some embodiments.

The present disclosure, in some embodiments thereof, relates to pulmonary delivery of a drug substance using a personal inhaler device and, more particularly, but not exclusively, to controlling flow through an inhaler.

In some embodiments, control of flow through the inhaler comprises dynamic control over the flow of ambient air. In some embodiments, an amount of drug substance that is delivered to the patient from a drug dose is controlled.

Overview

A broad aspect of some embodiments relates to controlled pulmonary delivery of one or more active substances of a drug dose to a user. In some embodiments, delivery is performed via a personal inhaler device.

An aspect of some embodiments relates to controlling conditions of airflow and/or temperature around, in and/or through a drug dose to achieve a targeted profile of release of a drug substance from the drug dose. In some embodiments, a targeted profile comprises a target temperature, range of temperatures, and/or time-evolving temperature or range of temperatures which the drug dose is heated to. Optionally a targeting profile comprises heating effected intermittently. Additionally or alternatively, a targeted profile comprises a targeted profile of flow, for example as described hereinbelow. In some embodiments, a targeted profile comprises a function, lookup table, or other description indexing flow and temperature characteristics together. For example, in some embodiments, as airflow increases, more of the heat delivered to a drug dose for drug substance vaporization is potentially drawn away. Optionally, a targeted profile of release (for example to achieve a particular rate of release) specifies that as an airflow increases, so does a delivery of heat. A potential advantage of this is to allow a more concentrated release of drug substance, while preventing overheating which could cause damage to the device, the drug substance, and/or injury to the user.

In some embodiments, a longer release time is targeted. Optionally, heating is maintained to a level which keeps a temperature of the drug dose just above a minimum effective vaporizing temperature, for example, within 1° C., within 2° C., within 5° C., within 10° C., or within another higher, lower or intermediate temperature above a minimum effective vaporizing temperature. Effective vaporizing is at a rate, for example, of 10% of the total dose substance per second, 20%/s, 30%/s, 50%/s, or another higher, lower, or intermediate Lower airflow is adjusted for by lowering the heating.

In some embodiments, heating and flow rate control are adjusted to compensate for limits in the range of control that each other allows. For example, as heating control reaches a limit of available power, flow is increasingly restricted, to prevent over-cooling of the drug dose. Additionally or alternatively, limits to the level of flow (for example, a minimum flow to ensure good transfer of drug substance to the user) are set, and the delivery of heat is regulated.

In some embodiments, a release profile is matched in terms of operational parameters. For example, a release profile which targets releasing all of a drug substance of a drug dose over a period of 2 seconds is defined in terms of operational parameters which heat the drug and/or control flow so that the 2 second release time target is matched. The operations parameters are determined, for example, empirically, and/or by use of models comprising known characteristics of the drug substance and/or the drug dose.

In some embodiments one or the other of the control possibilities is used dominantly for control of a target profile of release. For example, carrier flow is left substantially unregulated, while heating is varied to maintain a target temperature. Alternatively, heating is substantially constant, while carrier flow is regulated to produce an even (or other targeted) flow.

An aspect of some embodiments relates to controlling heating of a drug dose according to a sensed temperature indication and a targeted profile. In some embodiments, temperature is measured by, for example, an infrared sensor, and/or by a contact thermal sensor. Optionally, the temperature indication is calibrated to a temperature in degrees. Additionally or alternatively, the temperature indication is used operationally to set a particular level of heating. It is a potential advantage to control temperature based on sensed feedback, to help ensure that a targeted profile of drug substance release is met.

An aspect of some embodiments relates to controlling carrier gas flow (for example, airflow; also referred to as "carrier airflow" herein) through or adjacent a drug dose according to a determined profile, by providing shunting airflow based on a difference between an estimated flow through the drug dose, and the targeted profile of flow through the drug dose. In some embodiments, a volumetric flow rate through the drug dose is measured or estimated, for example using one or more sensors; and a flow of a gas (optionally, flow of ambient air), is dynamically modified based on the indication from the sensor(s). In some embodiments, when flow of shunting air into the inhaler device is prevented, the flow rate through the drug dose is equivalent to an inhalation flow rate of the user. It should be understood that the control of flow rate is optionally co-regulated with temperature control, for example as described hereinabove.

In some embodiments, an inhalation flow rate of the user is estimated in accordance with an indication provided by the one or more sensors. Optionally, the indication from the one or more sensors is combined with a current opening status of one or more valves that control the flow into and/or out of and/or within the inhaler device.

In some embodiments, for example, where natural fluctuations in the inhalation flow rate of a user occur potentially over a use session, airflow control includes dynamically modifying the flow of shunting airflow and/or shunting airflow relative to carrier airflow. This allows supplying the user with a flow rate at least partially governed by the act of inhalation (for example, not oversupplied with respect to a rate of inhalation), while maintaining the flow rate through the drug dose at an essentially fixed rate and/or within a specific profile.

In some embodiments, dynamic modifying of flow is effected to achieve and/or maintain a target profile of flow through the drug dose. Optionally, a target profile comprises or consists of maintaining the flow through the drug dose at a constant rate; for example, 0.5 L/min, 1 L/min, 4 L/min, or an intermediate, higher or lower rate of flow. Optionally, the profile of flow through the drug dose comprises a varying flow profile, for example including a linearly increasing rate, linearly decreasing rate and/or any other profile.

The term "target profile" as used herein means a pattern of features of airflow through an inhaler device, including one or more of: a rate of flow, a period of flow, and a distribution of flow between different conduits and/or different tracts of the device. A target profile optionally includes a plurality of target profiles, and optionally the timing, duration, and/or a degree of overlap between such target profiles. For example: a device having a plurality of conduits, at least one of which provides passage through a drug dose, optionally has a target profile including a period during which at least one (sub-) target profile is imposed on flow through the drug dose and at least one other (sub-) target profile is defined by a degree of drag, obstruction, and/or flow resistance imposed on inhalation flow drawn by a user through the device.

Optionally a target flow profile through the drug dose is selected to control an amount of drug substance released, control timing of drug substance delivery, to set an inhalation depth, to target a location for drug delivery within the body of the user, and/or control a profile of active substances released from the drug dose (for example by selecting a flow profile that will initially release a first drug substance and only at a later stage of inhalation release a second drug substance). In some embodiments, more than one drug dose substrate is contained within a drug dose cartridge of the inhaler device. Optionally, release of one or more drug substances is controlled in accordance with a size (e.g. molecular size), weight, or another chemical or physical property of a drug substance.

In some embodiments, commencement of inhalation is detected, for example when the measured inhalation flow rate is above a predefined threshold. Optionally, this threshold is a flow rate through the drug dose which is equal to the value that is to be maintained for at least part of a target flow pattern. In some embodiments this is a value that is to be maintained (constantly or intermittently) for at least 0.25 or even 0.5 seconds. In some embodiments this rate is 0.5 L/min, 1 L/min or even 2 L/min, or an intermediate rate of flow.

Optionally, commencement of inhalation triggers activation of drug substance release. In some embodiments, drug substance release involves processing of the drug dose, for example by heating the drug dose to extract one or more active substances. In some embodiments, the drug dose comprises plant material, for example *cannabis* and/or tobacco, and an active substance (e.g. THC and/or nicotine) is extracted by heating the plant matter. Other examples for plant material include one or more of *Cannabis sativa, Cannabis indica, Cannabis ruderalis, Acacia* spp., *Amanita muscaria, Yage, Atropa belladonna, Areca catechu, Brugmansia* spp., *Brunfelsia latifolia, Desmanthus illinoensis, Banisteriopsis caapi, Trichocereus* spp., *Theobroma cacao, Capsicum* spp., *Cestrum* spp., *Erythroxylum coca, Solenostemon scutellarioides, Arundo donax, Coffea arabica, Datura* spp., *Desfontainia* spp., *Diplopterys cabrerana,* *Ephedra sinica, Claviceps purpurea, Paullinia cupana, Argyreia nervosa, Hyoscyamus niger, Tabernanthe iboga, Lagochilus inebriens, Justicia pectoralis, Sceletium tortuosum, Piper methysticum, Catha edulis, Mitragyna speciosa, Leonotis leonurus, Nymphaea* spp., *Nelumbo* spp., *Sophora secundiflora, Mucuna pruriens, Mandragora officinarum, Mimosa tenuiflora, Ipomoea violacea, Psilocybe* spp., *Panaeolus* spp., *Myristica fragrans, Turbina corymbosa, Passiflora incarnata, Lophophora williamsii, Phalaris* spp., *Duboisia hopwoodii, Papaver somniferum, Psychotria viridis,* spp., *Salvia divinorum, Combretum quadrangulare, Trichocereus pachanoi, Heimia salicifolia, Stipa robusta, Solandra* spp., *Hypericum perforatum, Tabernaemontana* spp., *Camellia sinensis, Nicotiana tabacum, Nicotiana rustica, Virola theidora, Voacanga africana, Lactuca virosa, Artemisia absinthium, Ilex paraguariensis, Anadenanthera* spp., *Corynanthe yohimbe, Calea zacatechichi, Coffea* spp. (Rubiaceae), *Sapindaceae* spp., *Camellia* spp., *Malvaceae* spp., *Aquifoliaceae* spp., *Hoodia* spp. *Chamomilla recutita, Passiflora incarnate, Camellia sinensis, Mentha piperita, Mentha spicata, Rubus idaeus, Eucalyptus globulus, Lavandula officinalis, Thymus vulgaris, Melissa officinalis, Tobacco, Aloe Vera, Angelica, Anise, Ayahuasca* (*Banisteriopsis caapi*), Barberry, Black Horehound, Blue Lotus, Burdock, Camomile/Chamomile, Caraway, Cat's Claw, Clove, Comfrey, Corn Silk, Couch Grass, Damiana, Damiana, Dandelion, *Ephedra, Eucalyptus*, Evening Primrose, Fennel, Feverfew, Fringe Tree, Garlic, Ginger, Ginkgo, Ginseng, Goldenrod, Goldenseal, Gotu Kola, Green Tea, Guarana, Hawthorn, Hops, Horsetail, Hyssop, Kola Nut, Kratom, Lavender, Lemon Balm, Licorice, Lion's Tail (Wild Dagga), Maca Root, Marshmallow, Meadowsweet, Milk Thistle, Motherwort, Passion Flower, Passionflower, Peppermint, Prickly Poppy, Purslane, Raspberry Leaf, Red Poppy, Sage, Saw Palmetto, Sida Cordifolia, Sinicuichi (Mayan Sun Opener), Spearmint, Sweet Flag, Syrian Rue (*Peganum harmala*), Thyme, Turmeric, Valerian, Wild Yam, Wormwood, Yarrow, Yerba Mate, and/or Yohimbe. The dosing botanical substance optionally includes any combination of plant material from this list, and/or other plant material. Optionally, the drug dose comprises one or more synthetic or extracted drugs added to or applied on carrier material, wherein the added drug and/or the drug dose may be in the form of or comprise solid material, gel, powder, encapsulated liquid, granulated particles, and/or other forms. In some embodiments, the drug dose comprises plant material having one or more synthetic or extracted drugs added thereto or applied thereon.

In some embodiments, a structure of the personal inhaler device includes one or more first conduits within which air entering the inhaler device flows through the drug dose; at least one second, shunting conduit in pneumatic communication with the first drug conduit, through which shunting airflow (which avoids the drug dose itself) may be allowed to join the flow that had already passed through the drug dose; optionally a third, bypass conduit through which ambient air (e.g. a flow not carrying a drug substance) may be allowed to flow directly to the user; and a regulating mechanism for controlling flow through the one or more conduits, for example comprising one or more valves. Optionally, air flows into the first conduit in response to pressure reduction produced in the device during inhalation. In some embodiments, the first conduit(s) together with the second, and/or third conduit(s) join to produce a combined flow. Optionally, two or more of the conduits unite in proximity to and/or within the mouthpiece of the inhaler device. It is to be understood that an "at least one first conduit" (or second or third conduit, and/or drug, shunting, or bypass conduit) is also equivalently referred to herein as "a first" (or other) "conduit comprising at least one tract". Thus, for example, a single conduit for one of the drug substance-bearing, shunting, or bypass airflow functions is optionally comprised of two, three, or more tracts.

In some embodiments, at least one flow rate sensor is positioned within the device, at a location suitable to detect a rate of flow that passed through the drug dose, for example being positioned within the drug conduit distally to a connection between the shunting conduit and the drug conduit. In some embodiments, input from the sensor is received on a controller of the inhaler device, which in turn operates the one or more valves accordingly. In an example of operation of the device: if the target flow rate through the drug dose comprises a constant rate of 1 L/min, and the sensor detects a flow rate of 3 L/min through the drug dose, the controller will open at least one shunting conduit to allow ambient flow at a rate of 2 L/min into the drug conduit, thereby reducing the upcoming flow rate through the drug dose to the target 1 L/min, while still providing the user with a rate of 3 L/min, similar to the inhaled rate. A valve which operates to control a flow rate through a drug carrier conduit by a relative opening or closing which controls a flow rate in a shunt conduit is termed a "shunt valve" herein. A shunt valve is optionally located within a shunt conduit; additionally or alternatively, it is located in a drug conduit.

An aspect of some embodiments relates to a sequence of flow manipulations through an inhaler device, which provides a perceptible indication to a user. In some embodiments, the sequence of flow manipulations comprises a significant reduction in the flow through the device, optionally to a full obstruction, which is optionally followed by allowing resumed flow. Optionally allowing resumed flow includes allowing a rapid flow, being significantly faster than before the reduction.

In some embodiments, the partial obstruction of flow includes obstructing all flow through the device other than flow through drug dose, to flush residual released drug substance into and/or from the conduit. Optionally, the partial obstruction of flow includes a full obstruction (or almost full), in which all conduits are blocked to significantly reduce pressure in the conduits, enough to be sensed by the user. Potentially, by attempting to inhale against partial or full obstruction, a user naturally increases inhalation effort, creating increasingly negative pressure within the device. Optionally, the partial obstruction is followed or replaced by the full or almost full obstruction.

In some embodiments, a rapid pulse of flow is allowed by opening at least the bypass (third) conduit, to allow ambient airflow directly to the user. Additionally or alternatively, the drug conduit and/or the shunting conduit are opened as well. In some embodiments, when rapid flow is allowed, drag forces are reduced, reducing a resistance encountered by the user when inhaling through the device. Optionally, reduction of drag forces is obtained by allowing the rapid flow through an opening having a cross sectional area substantially larger than the cross sectional area through which drug substance infused flow was provided. In some embodiments, the pulse of flow includes a total volume which is about equal to or even larger than an anatomic dead space of the user, for example 150 ml or larger, chasing the drug substance deeper into the lungs, potentially ensuring deep lung delivery, and/or reducing the amount of drug substance exhaled immediately after using the inhaler.

An aspect of this disclosure relates to producing circumferential airflow when delivering a drug substance through a conduit, in which flow comprising a higher drug substance concentration is surrounded by flow comprising a lower drug substance concentration. This may be seen as a "sleeve-like" effect of laminar flow wherein the circumferential airflow flows around air that passed through the drug dose with little mixing, thereby reducing contact of released drug substances with conduit walls. In some embodiments the sleeve-like effect is obtained by allowing entry of shunting flow, for example through the shunting conduit(s), into the first conduit to join carrier airflow that has already passed through the drug dose. For example, the flow through the shunting conduit(s) is provided through a plurality of openings surrounding the conduit. Optionally, this is performed uniformly around the central flow, to reduce turbulence in the combined flow. In some embodiments, flow rate is controlled to keep flow in a laminar (substantially non-turbulent) flow regime, at least near the conduit walls. For example, flow velocity leading to a Reynolds number of 2100 or less is maintained. However, it is to be understood that the critical Reynolds number below which flow maintains laminar characteristics varies according to the particular geometry of the conduit.

In some embodiments, a double sleeve-like effect is obtained by allowing more ambient flow at positions more proximal than the aforementioned. This may be performed, for example, by having two or more sets of tracts of the shunting conduit(s) which provide ambient air sequentially along the flow path. Additionally or alternatively, a double sleeve-like effect is obtained by opening the bypass conduit(s) so that at least at a proximal portion of the mouthpiece all flow is united, while the air with the highest drug substance concentration flows through a substantially center of the conduit.

A potential advantage of a sleeve-like effect may include reducing adherence of drug dose residues and/or active substances to the walls of the conduit, which may be especially advantageous when the drug dose comprises oily materials, for example comprising plant material such as *cannabis*.

An aspect of some embodiments is the control of an inhaler device to produce changes in a flow profile (for example, a flow profile which adjustably regulates flow through a plurality of conduits) by the movement of a mechanism which provides control over two or more valves at once. In some embodiments, the mechanism comprises at least two apertured elements, for example, at least two disks or at least two cylinders. Movement (for example, rotation and/or straight line translation) of one apertured element relative to the other element changes the relative alignment of the apertures. Optionally, apertures are arranged so that a plurality of valves (for example, valves to a carrier conduit) are opened and closed together by a single movement. Optionally, apertures are arranged so that at least one valve opens while another valve closes. Optionally, apertures are arranged so that valve opening and closing can be performed relatively separately among two or more valves, depending on the motion and/or relative position of the valve members.

As used herein, the term "ambient air" includes air entering a conduit of the device. Ambient air optionally comprises room air or any modification thereof, such as addition of one or more drug substances to the air, humidification of the air, and/or other modifications. Optionally, ambient air relates to air that flows to the user via a conduit without passing along or via the drug dose.

Herein, the term "proximal" is used in reference to a portion, component and/or opening of the inhaler device in relative proximity to the user end during an inhalation event, e.g. a mouthpiece. A component may be physically "distal" or "proximal", and/or it may be at a position that is relatively more distal or proximal than another position. For example, the term "distal" is used in reference to a portion, component and/or opening of an inhaler device which is closer to an end of the device opposite the user end. Optionally, a component is described as functionally or operationally "distal" or "proximal". For example "distal" could be used in reference to a conduit opening through which air initially enters the device, before advancing through the path of flow to the user, regardless of the physical position of the opening with respect to the user end.

As used herein, the term "drug substance" or "active substance" is used in reference to one or more pharmaceutically or otherwise active substances, for example therapeutic or medicinal substances and/or substances for recreational use, and/or substances for testing. In some embodiments an "active" substance is such substance which may have an effect on a user's body or any part thereof. A "drug substance" may be administered to a user, for example by vaporization, suspension, and/or volatilization of the drug substance into gas (typically air) inspired by a user. Optionally, a drug substance includes one or more non-active materials accompanying the active portion of the drug substance.

The term "drug dose" denotes material, arranged for use in an inhaler device, from which one or more drug substances are released (e.g. extracted or vaporized). In some embodiments the material comprises the one or more drug substances. A drug dose is optionally arranged, for example, as a pallet of the drug dose material. The terms "drug cartridge" and "drug repository" include structures that are configured for the handling and/or structure maintenance of a drug dose (for example, for supporting a drug dose pallet), including, for example, one or more of: a carrier, housing, frame, packaging, or other structure associated with the drug dose material itself; this is also referred to as a "dose unit" or "drug dose unit". Optionally, the drug dose together with all additional structures is configured to permit airflow through the drug dose at least at a rate of 0.5 L/min, 1 L/min, 4 L/min, or an intermediate, higher or lower rate of flow.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Figure 1B:
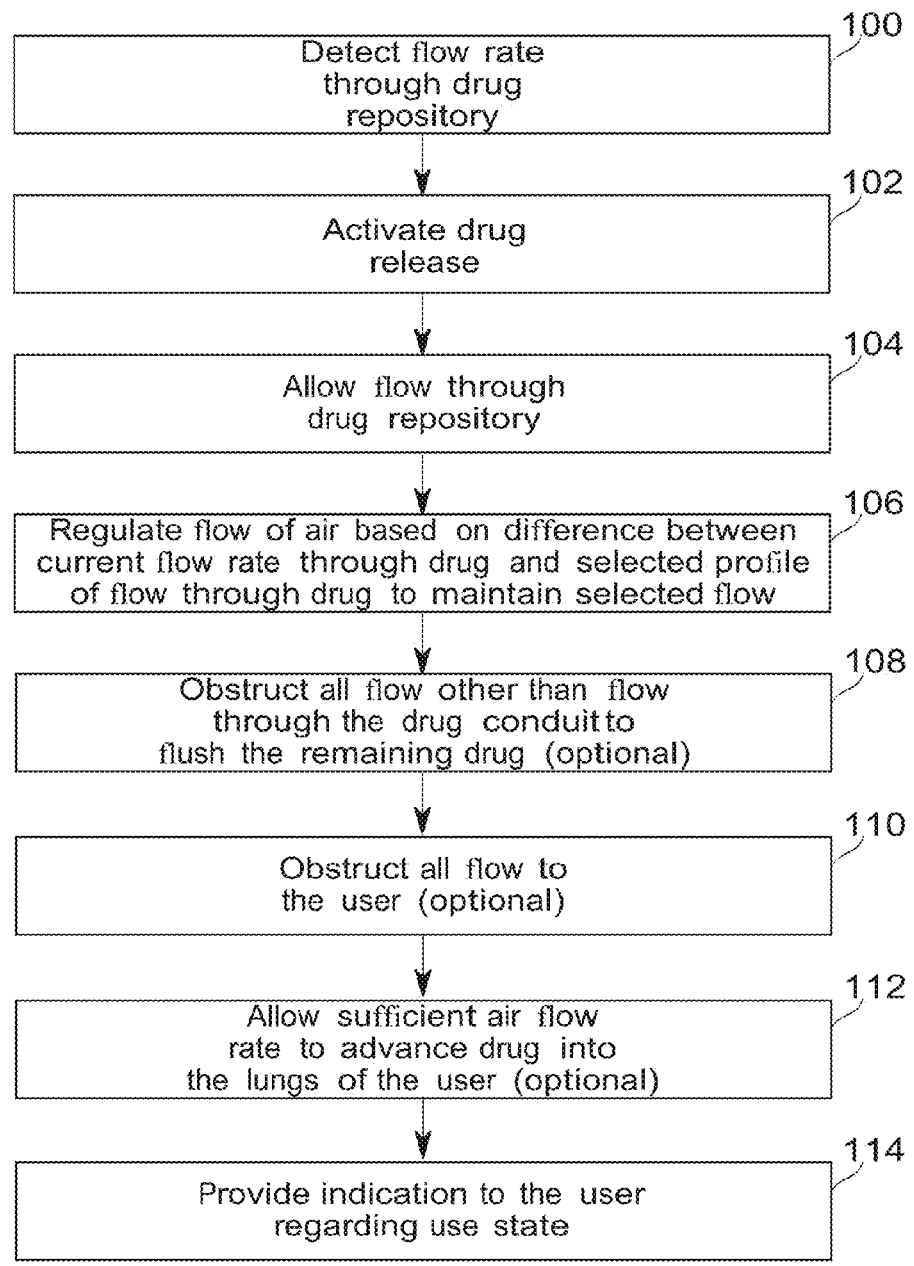

Reference is now made to FIGS. 1A-1B, which are schematic flowcharts of general (FIG. 1A) and detailed (FIG. 1B) methods for pulmonary delivery of one or more drug substances to a user using an inhaler device, according to some embodiments of the invention.

FIG. 1A is a general method of controlling flow through an inhaler device. In some embodiments, as further detailed below, a target profile of air flow through the drug dose is optionally selected (block 120). In some embodiments, selecting the target profile comprises selecting one or more parameters such as flow rate, total volume, duration, flow velocity, and/or other parameters of the flow that passes through the drug dose and/or through one or more conduits of an inhaler device. In some embodiments, a target profile is selected prior to providing the drug substance to the user through the inhaler device (for example, during manufacturing of the device, and/or during a previous configuration of the device). Additionally or alternatively, the profile is selected and/or modified during a use session, for example during an inhalation of the user through the inhaler device. Additionally or alternatively, the profile is selected before a new use (e.g. use by a different user and/or for a different drug substance or different drug substance concentration). Optionally, the profile is determined in the process of design or manufacture of the device, such that the device can operate only according to the predefined profile without necessarily performing an act of selection during use.

In some embodiments, to maintain flow (e.g., carrier airflow) through the drug dose at the target profile, shunting air flow into the device is dynamically controlled according to an estimated flow through the drug dose and the target flow profile through the drug dose (block 122). In some embodiments, shunting air flow unites with flow that had already passed through the drug dose. In some embodiments, shunting flow is allowed into the inhaler device (for example by opening a valve) in response to a difference between the estimated flow through the drug dose, and the target flow profile through the drug dose.

The following method, for example as described in FIG. 1B, is optionally used for inhalation of pharmaceuticals or any other drug substances using a personally operated inhaler device. In some embodiments, an inhaler device suitable for implementation of a method, for example as described herein, comprises at least a first conduit through which one or more active substances are delivered to the user (the first conduit will be hereinafter referred to as "drug conduit"). This drug conduit passes through a drug repository where the drug substance or one or more active substances are added to air flowing through the repository; a second conduit that joins the drug conduit at a more proximal location along the drug conduit, in which air has already flown past the drug repository, allowing ambient air to enter and join the drug substance-infused air that passed via the repository, thereby increasing a volume of the air flowing through the drug conduit (the second conduit will be hereinafter referred to as "shunting conduit"); optionally a third conduit conducting ambient air directly to the user (the third conduit will be hereinafter referred to as a "bypass conduit"); and one or more regulating means (for example valves), for controlling flow into the inhaler device, flow through the conduits and/or in between the conduits, and/or flow out of the inhaler device.

In some embodiments, the drug conduit and the bypass conduit lead the flow to a common passage, for example a passage through the mouthpiece. In some embodiments, the method comprises detecting a flow rate through a drug repository. In some cases, for example when entry of flow into conduits other than the drug conduit(s) is prevented, flow rate through the drug dose (also termed drug repository) is indicative to the inhalation flow rate of a user (block 100). In some embodiments, flow rate is detected by one or more sensors, for example a differential pressure sensor. Additionally or alternatively, flow rate is sensed and/or adjusted mechanically, for example using pressure release valves, duck billed valves, and/or the like.

In some embodiments, commencement of inhalation is detected, for example by measuring a flow rate that is above a defined threshold. In some embodiments, a flow rate is measured continuously during inhalation. Alternatively, a flow rate is measured occasionally or periodically during inhalation; for example: every 10 msec, every 50 msec, every 100 msec, every 500 msec, every second, or over intermediate, longer or shorter time periods. In some embodiments, flow rate measurement is performed within the drug conduit, at a location distal to a junction between a shunting conduit and a drug conduit.

In some embodiments, drug substance release is activated (block 102). Optionally, commencement of inhalation triggers activation (e.g. when a sensed flow rate is significantly greater than zero). In some embodiments, drug substance release is activated only when air flow through the drug dose is sensed to be above a higher threshold. Optionally this threshold equals a flow rate through the drug dose that is maintained constant for at least a portion of an inhalation event. In some embodiments, this threshold is 1 L/min, 0.5 L/min, 2 L/min, or an intermediate, higher or lower flow rate. In some embodiments drug substance release is activated additionally or alternatively subject to being prompted by a user, for example by pressing a button or shifting the inhaler device to a ready-to-use position.

In some embodiments, activation of drug substance release comprises evacuating one or more active substances of the drug dose. Optionally, evacuation comprises one or more of heating, vaporizing, initiating a chemical reaction, changing a physical state of the drug dose material (e.g. turning to aerosol), simply allowing air to flow through the drug repository and carry the drug substance, and/or other methods suitable for releasing and/or extracting the drug substance to deliver it to the user. Optionally, drug substance release is activated for a defined time period. Alternatively, drug substance release is activated for a time period which is dynamically adjusted, for example based on the flow rate measurement.

In some embodiments, air entering the inhaler in response to suction produced in the device during inhalation flows through the drug conduit, passing the drug repository (block 104). Optionally, all other conduits are obstructed at this stage.

In some embodiments, a target flow profile through the drug repository is maintained by regulating flow of ambient air (block 106), such as air entering through the shunting conduit. In some embodiments, flow of ambient air is regulated based on differences between the current flow rate through the drug dose, as detected for example by the pressure sensor, and the target flow rate through the drug dose.

In some embodiments, a target flow profile through the drug dose comprises or consists of a constant flow rate, for example 1 L/min, 0.5 L/min, 2 L/min, or an intermediate, higher or lower flow rate, optionally for a certain period of time. Additionally or alternatively, a target flow profile comprises an increasing or decreasing flow rate. Optionally, the change in flow rate is monotonic. Optionally, the change in flow rate is linear. Additionally or alternatively, a target flow profile comprises other profiles, such as one or more of constant flow through the drug dose followed by unregulated flow through the drug dose (optionally with all other conduits closed); constant flow through the drug dose followed by allowing of rapid flow through the bypass conduit(s); constant flow through the drug dose followed by a partial or full obstruction of the conduits, and/or other profiles or combinations thereof and any other flow profile described herein.

In some embodiments, the target flow profile is set in accordance with one or more of the following parameters: the type of drug dose and/or substance, the amount of drug dose and/or substance, the time period required to release the drug substance, the type of processing of the drug dose (e.g. heating), and/or user parameters. For example, for a user (e.g. a small child) that cannot inhale more than 500 ml/min, flow through the drug dose may be adjusted to a set maximal and/or constant value of 500 ml/min. In another example, a user suffers from shortness of breath, and though capable of inhaling a volume of, for example, 2 L/min, this is but for a limited time period, such as 2 seconds. Optionally, then, a rate of flow through the drug dose is set to a higher value, for example 1.5 L/min. This higher value may be set in order to deliver in the 2 second time period an amount of drug substance nearing that which would have been provided over, for example, a 3 second time period to a user capable of longer inhalation. Optionally, release of the one or more drug substances is accelerated, for example by modifying a heating profile. In some embodiments, a target flow profile through the drug dose contributes to quantifying and/or timing drug substance release.

In some embodiments, a target profile of flow through the drug dose is selected to increase control over the dosage of drug substance inhaled by the user. For example, if a strong suction force is produced in the device during inhalation, air flow at a relatively high velocity will enter the device and pass through the drug dose, possibly increasing the amount of drug substance released over a target amount. In an embodiment in which the drug dose is heated, flow at a higher velocity than the target may cause premature cooling of the drug dose. Therefore, by controlling a rate of airflow through a drug dose, the amount of drug substance inhaled from a dose unit having a given composition may be essentially the same for a wide range of users.

In some embodiments, regulating of ambient air flow comprises allowing flow through the shunting conduit(s) (e.g. by opening a valve to allow flow between the drug conduit and the shunting conduit and/or by controlling the extent to which it is opened) based on the measured inhalation flow rate. In some embodiments, a threshold for opening the shunting conduit comprises a detected inhalation flow rate that is higher by at least 1%, at least 5%, at least 20% or an intermediate, higher or lower percentage higher than an initial target rate of flow through the drug dose, such as a rate of 1 L/min.

In an example, if the target flow profile through the drug dose is set to a constant 1 L/min, and the user's initial inhalation flow rate is measured at 3 L/min (as sensed within the drug conduit, assuming other conduits are initially closed), the shunting conduit will open and allow air to enter at a flow rate of 2 L/min. The target constant profile will then be maintained by detecting a deviation in flow rate through the drug conduit (at a distal portion of the conduit, before the joining the shunting conduit) from 1 L/min, and dynamically regulating ambient flow through shunting conduit accordingly. Assuming natural fluctuations in the inhalation flow rate of the user, the "completing" ambient flow rate that is allowed into the device will vary at various time points during inhalation. In such cases, the sensed flow rate would be approximately equal to the difference between the user's inhalation flow rate and the flow rate through the shunting conduit. For example, if in the above case the user's inhalation increased to 3.5 L/min, and the flow rate via the shunting conduits was set to 2 L/min, then a flow rate of about 1.5 L/min would be sensed. In such case the shunting conduit will open further to allow air to enter at a flow rate of 2.5 L/min, thereby reducing the sensed flow rate back to about 1 L/min. Likewise, if the inhalation flow rate is reduced (e.g. to 2.5 L/min.) the shunting conduit will partially close so that air may enter at a flow rate of 1.5 L/min only.

A potential advantage of dynamic regulation of ambient flow based on the current rate of flow or estimation thereof and the target flow profile through the drug dose includes providing a user with total volume of ambient air mixed with drug substance-infused air which is equal to the volume inhaled by the user, thereby allowing different users to breathe differently through the inhaler without significantly affecting air flow via the drug repository, and consequently the amount of inhaled drug substance.

In some embodiments, if a measured flow rate through the drug dose which is indicative of the inhalation flow rate or a measured inhalation flow rate is lower than a threshold, for example being lower than the target flow rate required through the drug dose, such as less than 1 L/min in the example described above, drug substance release will not be activated. Optionally, the inhaler device will provide an indication to the user (e.g. by a light indication, sound indication, tactile indication, and/or other indication) to increase air intake during inhalation. If this is sensed at a later time during operation drug substance release may be terminated, for example if the flow falls below the threshold for at least a specific period of time.

Additionally or alternatively, a fan, a blower and/or other air pressure source is used with the inhaler to supply additional flow into the inhaler. This configuration might be specifically advantageous in an inhaler device used by weak users, elderly users, young children, and/or other users incapable of inhaling at a minimal flow rate for drug substance release. Optionally, the fan or blower is operable in reverse. Potentially this mimics the effect of a closed or partially closed valve, acting to increase apparent resistance to air flow through a conduit.

In some embodiments, drug substance is released over a selected time period. In some embodiments, the time period is a target time period, for example a constant time period, such as 3 seconds, 5 seconds, 1.5 seconds, or intermediate, longer or shorter time periods. In some embodiments, a time period for drug substance release (e.g. by heating the drug dose) is dynamically modified or determined during inhalation, for example based on the detected inhalation flow rate. In an example, if the inhalation flow rate of the user is slightly under a target flow rate required through the drug dose (for example 5%, 10%, or 20% smaller), the time period of drug substance release is lengthened, and/or the heating profile is adjusted, to compensate for the lower flow rate; for example, lengthened from 3 seconds to 3.5 seconds.

In some embodiments, optionally at the end of drug substance release or shortly thereafter, all flow other than flow through the drug conduit is obstructed (partially or completely), to flush the remaining drug substance and deliver it to the user (block 108). Optionally, flow through the shunting conduit is gradually restricted before optionally being fully obstructed, to increase flow through the drug dose. It is noted that flushing of the drug substance may also take place when other conduits are open, albeit possibly at a slower rate.

In some embodiments, flow to the user is partially or fully obstructed (block 110). In some embodiments, the blocking occurs at the termination of the inhalation (for example, the events described in relation to block 112 are skipped). In some embodiments, the obstruction duration and/or degree is predefined. Alternatively, the obstruction duration and/or degree is set dynamically, for example determined according to a measured flow rate and/or a measured negative pressure buildup in the device during the obstruction period. Optionally, the target duration of obstruction is, for example, according to the user's sensed inhalation flow rate, to be long enough to reduce the internal pressure within the device, optionally generating a vacuum strong enough to be sensed by the user and/or to produce a consequent rapid flow or volume (for example a volume larger than an anatomical dead space, such as 150 ml or larger) upon release of the obstruction. In some embodiments, an obstruction duration set for a user inhaling at a relatively high flow rate will be shorter than an obstruction duration set for a user inhaling at a relatively low flow rate. Potentially, the short duration obstruction in the higher flow rate user will be sufficient for generating suction strong enough to be sensed by the user, while the low flow rate user might need a longer time period to sense the suction.

At block 112, in some embodiments, flow is allowed through the device and to the user, optionally at a relatively high rate. This is optionally after obstruction such as described in relation to blocks 108 and/or 110. Alternatively, the resumed flow is allowed without a prior period of flow restriction. Optionally, the rate of the resumed flow is high enough to admit a relatively large volume of air to cause the drug substance inhaled before the obstruction to advance deeper into the lungs of the user. Optionally, at least the bypass conduit is opened (for example, by opening of a bypass valve, optionally under the control of a bypass valve controller 325) to allow general ambient air flow to the user without being restricted by the drag of the drug conduit. In some embodiments, the drug conduit and/or shunting conduit are opened as well. In some embodiments, the duration of the advancing phase of the method is limited by the lung capacity of the user. Optionally, the opening of pathways for the advancing is for a limited period of time, for example, less than 4 seconds, 3 seconds, 2 seconds, 1 second, or less than another greater, lesser, or intermediate period. Optionally, at least one of the first conduit, the second conduit and the third conduit are left open for a period of time that extends beyond the end of an inhalation session. In such case, the conduit(s) may close in response to an action taken by the user (e.g. shifting the inhaler device to a "closed" position and/or pressing or releasing a button and/or when a device is primed for a later inhalation event or when a new inhalation is sensed).

Optionally, opening the bypass conduit effectively increases a cross section (and/or lowers a flow resistance) of the mouthpiece relative to the effective cross section (and/or flow resistance) that exists when only the drug conduit and/or shunting conduit are open. The effective cross section may be taken to mean a cross section that defines the drag forces resisting the flow of air to the user. For example, the effective cross section may be taken to mean a minimal cross section through which the flow passes to the user. For example, this effective cross section may be the sum of the minimal cross sections of all conduits through which air flows at a given point. Optionally, the cross-sectional area of the bypass conduit is at least 25% larger than the cross-sectional area of the drug conduit, at least 50% larger, at least 100% larger, at least 200% larger, or larger by another greater, smaller, or intermediate factor.

Optionally, drag forces resisting flow to the user are reduced by the enlargement of effective cross section through the mouthpiece, allowing flow of higher velocity to the user at the same applied suction power. Optionally, the user senses a sudden decrease in resistance when breathing through the inhaler as compared to the relatively restricted breathing during drug substance release and/or during the obstruction period.

It is noted that in some embodiments, a full obstruction of flow optionally does not take place, and the bypass conduit is opened to allow ambient flow to the user to provide the large enough air pulse.

In some embodiments, an indication regarding the use state, for example regarding the inhalation state is provided to the user (block 114). Optionally, the indication is provided to indicate that a use session is completed, and the user may stop inhaling through the device. The indication optionally comprises, for example, a tone, vibration, and/or light. In some embodiments, the indication comprises direct lung-inhaler device feedback obtained during use. For example, a specific pattern of inhalation that is elicited from the user by the inhaler may be included in such indication. More particularly, the indication may include the sequence of actions including, for example, allowing flow during drug substance delivery, followed by a substantial reduction in flow, optionally to a full obstruction. Optionally the sequence includes a following resumed pulse of air, optionally at a higher velocity and/or reduced resistance relative to one or all the preceding flow periods in the sequence. In another example, the indication includes preventing air flow via the device at the end of the session, such that the high resistance is sensed by the user as an ending point. In some embodiments, a particular sequence of flow resistances experienced by the user indicates successful inhalation (for example, controlled flow/restricted flow/free flow), and any other pattern indicates a problem has occurs. In some embodiments, one or more distinct "warning patterns" are defined; for example, a fluttering pattern, a full flow stop pattern, or another pattern of modulated flow resistances. Optionally, an indication provided to a user by a pattern of flow resistances is combined with additional audio, visual and/or tactile indication. Potentially, this provides a more conventional indication to the user that, for example, clarifies the indication of the pattern.

In some embodiments, a "substantial reduction in flow" or "significant reduction in flow" means a reduction of the "rate of total airflow" to an inhaling user through the device. This "total airflow" relates to all flow of air through the device to the inhaling user, through all conduits, for example, a total volume flowing within a period of seconds, milliseconds, a single inhalation, or another period. Herein, "rate of airflow" is a material flow rate of gas (usually, but not only, derived from ambient air), for example, a volumetric flow rate of air. A "substantial reduction" in the rate of total airflow optionally includes any reduction that is sensed by an inhaling user and may include a reduction of, for example, airflow rate of 50% or more or even 75% or more or even complete or near complete obstruction with a reduction of at least 95% or even 100% in the rate of total airflow.

In some embodiments, the indication includes allowing flow during drug substance delivery under some resistance (e.g. drag on total airflow), followed by a release or significant reduction of the resistance (e.g. by opening a valve that allows bypass airflow that does not pass through a drag imposing constriction).

In some embodiments, the flow rate through a device after obstruction is removed or reduced is at least 25%-50% of the flow rate before obstruction, or is approximately equal to the flow rate before obstruction. In some embodiments, the flow rate through a device after obstruction is removed or reduced (or before the change in resistance) is at least 25% larger than before obstruction (or before the change in resistance) or 50% larger, at least 100% larger, at least 200% larger, or larger by another greater, smaller, or intermediate factor.

In some embodiments a higher allowed flow rate after obstruction or resistance is removed (or reduced) may be advantageous in facilitating faster and/or deeper and/or a higher volume of inhalation Additionally or alternatively, indication to the user is provided by a visual indication (e.g. a LED indication), a tactile indication (e.g. a vibration in the inhaler device), an audible indication, and/or any other indication.

Figure 2:
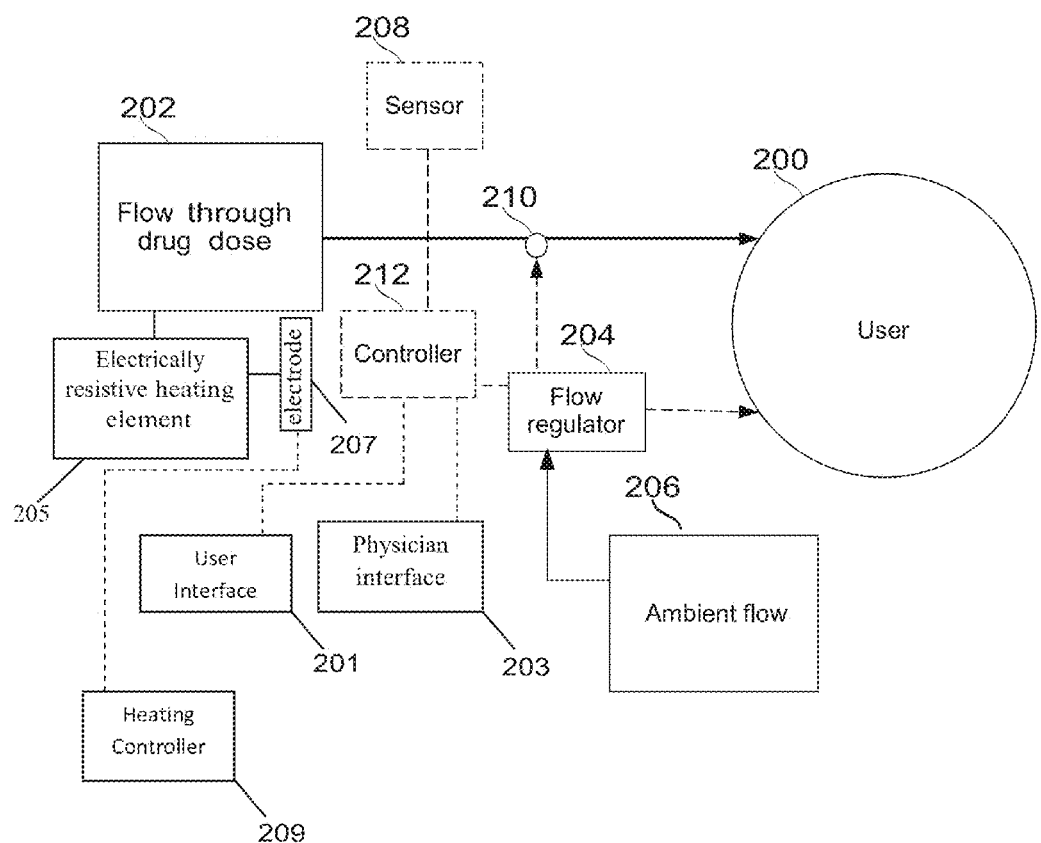
FIG. 2 is a schematic diagram of controlled flow through an inhaler device, according to some embodiments.

Reference is now made to FIG. 2, which is a schematic diagram of controlled flow through an inhaler device, according to some embodiments of the invention.

In some embodiments, flow throughout the inhaler device can be generally divided into three main flow paths: a first path of flow through the drug dose; a second optional path of ambient air flow that joins the first flow path; and a third optional flow path of ambient air that flows to the user without significantly affecting flow via the first flow path, for example by being provided directly to the user. In the schematic diagram shown herein, inhalation of user 200 produces suction in the device, causing air to enter the device. In some embodiments, airflow 202 entering the device flows through the drug dose. The drug dose and/or drug cartridge comprising the drug dose is held in position by a holder of the inhaler device. The holder is configured to hold the drug dose or a drug cartridge comprising the drug dose such that at least 90% of the carrier airflow passes through the drug dose. In some embodiments, at least 98% or even 100% of the carrier airflow passes through the drug dose. For example, the holder may position a dose unit within a tract of the drug conduit and seal airflow around the drug dose, such that only (or mostly) airflow that passes through the drug dose reaches the mouthpiece. Optionally, the sealing prevents airflow from contacting sensitive mechanical and/or electrical components of the inhaler. To control a rate of flow through the drug dose 202, optionally according to a target profile, a flow regulator 204 is positioned to dynamically govern ambient flow 206 into the inhaler device. In some embodiments, ambient air that entered the device is directed to join the flow that has already passed through the drug dose (via the second or shunting flow path). Additionally or alternatively, ambient air that entered the device flows directly to user 200 (via the third or bypass flow path).

In some embodiments, regulation of ambient flow 206 is performed based on a sensed flow rate which is determined at least partially by an inhalation force applied by user 200. Additionally or alternatively, regulation of ambient flow 206 is performed based on a difference between an actual rate of flow through the drug dose, and a target rate of flow through the drug dose. Optionally, a rate of flow through the drug dose or an indication thereof is sensed by a sensor 208, configured for example distally to juncture 210 in which ambient flow 206 or part thereof joins the flow that has already passed through the drug dose. In some embodiments, when all paths other than the drug substance extraction flow path are obstructed, a rate of flow through the drug dose indicates the inhalation flow rate of the user. This indication may be acquired, for example, at the beginning of a use session, to detect commencement of inhalation, for example by measuring flow rate above a certain threshold.

In some embodiments, when the detected flow rate through the drug dose is higher than a target flow rate through the drug dose (the target rate), flow regulator 204 permits ambient flow 206 or part thereof to join the flow that has already passed through the drug dose. As the user continues to inhale, the upcoming flow rate through the drug dose is reduced (as the flow that forms the "difference" between the target flow and the detected flow is allowed to enter through the ambient flow path).

In some embodiments, as inhalation continues, and if ambient flow is already allowed into the device, the sensor will detect a rate of flow through the drug dose, which may be different than the inhalation flow rate. Optionally, when a flow rate through the drug dose that is higher or lower than certain target is detected, the rate of ambient flow into the device will be dynamically modified to reduce or increase the upcoming rate of flow through the drug dose to the target value.

A potential advantage of the flow control mechanism described herein may include providing the user with a flow rate that is similar to the inhalation flow rate, while maintaining flow through the drug dose at a target profile, optionally without significantly affecting the amount of drug substance that is inhaled by the user.

In some embodiments, flow regulator 204 permits ambient flow 206 to pass to the user without affecting the flow rate through the drug dose (e.g. directly to the user), at least for a portion of a use session. Optionally, such ambient flow is provided to the user in parallel to the providing of flow that passed through the drug dose and/or in parallel to a mixture of flow that passed through the drug dose and ambient flow. Alternatively, ambient flow without affecting the flow rate through the drug dose is provided separately, for example when providing the user with an air pulse to advance the drug substance into the lungs, such towards the end of a use session.

In some embodiments, flow regulator 204 is configured to control a profile of the ambient flow (e.g. control one or more of a rate, velocity, pressure, volume and/or other parameters). Optionally, the flow is controlled by dynamically modifying a cross sectional area of a passage through which the ambient air enters the device and/or advances within the device, such as a by valve that is shaped to allow free flow and/or partial flow and/or no flow through the passage.

In some embodiments flow regulator 204 is mechanical and reacts autonomously to perceived pressures. In such cases, in some embodiments, a flow controller separate from the regulator itself is not included in the device.

In some embodiments, flow regulator 204 is activated by a controller 212. Optionally, controller 212 is programmed to receive an indication from sensor 208, such as an indication of flow rate through the drug dose, and to activate regulator 204 accordingly. In an example, sensor 208 provides an indication of flow rate that is higher than a target flow rate through the drug dose, and controller 212 activates flow regulator 204 to permit entry of ambient flow 206, such as by at least partially opening a valve.

In some embodiments, the inhaler device comprises one or more additional flow sensors, such as a sensor configured within a shunting conduit to detect parameters (e.g. flow rate) of the ambient flow entering through the shunting conduit to join the flow in the drug conduit, a sensor configured within a bypass conduit to detect parameters (e.g. flow rate) of the ambient flow entering the device, a sensor configured within the mouthpiece to detect parameters of flow exiting the device, optionally collecting data of a total volume of flow provided to the user, such as during a use session.

In some embodiments, a measure of inhalation volume, such as by the one or more sensors of the inhaler device, can be used as an indication of a physiological condition of the user, such as pain level. It is suggested that when a user is experiencing breakthrough pain, relatively high inhalation volumes may be observed. In some embodiments, an amount of drug substance provided to the user is modified based on the detected inhalation, optionally in real time.

In some embodiments, controller 212 is configured for storing data received from the one or more sensors. In some embodiments, controller 212 is configured to transmit data such as parameters of inhalation, a total volume of flow that was provided, parameters of flow that passed through the drug dose, and/or other parameters which were received as input on the controller to a user interface 201 and/or to a physician interface 203. Optionally, the user interface is configured on a hand held device, such as a smart phone, smart watch/band, personal computer, and the like. Additionally or alternatively, data is communicated to the user through the inhaler device, for example presented on a screen mounted on an external housing of the device and/or via telemetry to a separate device.

In an example, if the user inhales at a rate which is lower than a threshold required for activating drug substance release, the inhalation flow rate will be detected by the one or more sensors, which in turn will signal the controller, which in turn will provide an indication to the user to increase inhalation effort. Additionally or alternatively, the controller will operate a fan, a blower and/or other pressure source to supply the required flow, compensating for the low inhalation rate of the user. In another example if the user inhales at a rate which is lower than a threshold required for activating drug substance release, the device will not activate drug substance release and a notification may be provided to the user.

In some embodiments, a heating controller 209 is configured to control heating of the drug dose to release one or more drug substances, for example via an electrode 207 configured to apply an electric current to an electrically resistive heating element 205 which is arranged to heat the drug dose substantially without blocking airflow through.

Figure 3:
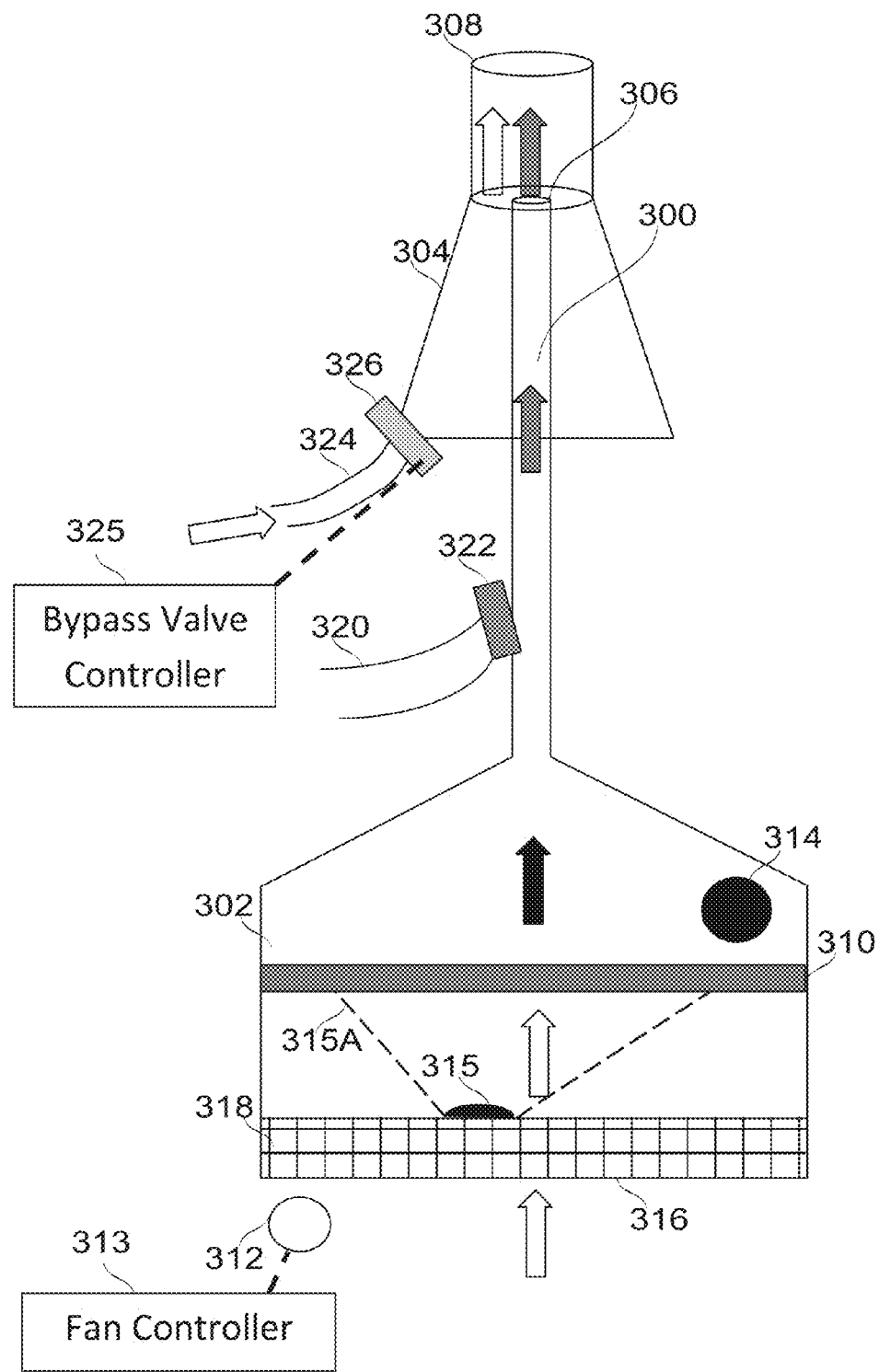
FIG. 3 is a schematic illustration of components of a flow control system, for example as incorporated within an inhaler device, according to some embodiments.

Reference is now made to FIG. 3, which is a schematic illustration of components of a flow control system, for example as incorporated within an inhaler device, according to some embodiments of the invention.

In some embodiments, the system comprises a conduit 300 for delivery of one or more active substances of a drug dose. In some embodiments, conduit 300 extends from a chamber 302 attached to the conduit at a position distal to the user, to (or optionally through) a mouthpiece 304 positioned at a proximal end of the conduit. Conduit 300 ends with an opening 306 through which the drug substance exits the conduit in the direction of a user.

In some embodiments, conduit 300 is shaped and/or sized to produce a drag force which increases a resistance to inhalation of the user. For example, a relatively small cross-sectional area of opening 306 of conduit 300 increases drag. Optionally, the resistance is sensed by the user, and might induce the user to increase inhalation efforts.

In some embodiments, chamber 302 comprises a drug repository 310. The drug repository is held in position within the device by a holder. A drug dose within repository 310 may be in to the form of solid material, gel, powder, encapsulated liquid, granulated particles, and/or other forms. Optionally, the drug dose is processed within the device before it is provided to the user, for example to extract one or more active substances, for example by heating. In some embodiments, drug repository 310 includes plant material, for example *cannabis* and/or tobacco, from which one or more active substances such as THC and/or nicotine are extracted, for example as further described herein. In some embodiments, for example when the drug dose comprises plant material, a smoke-like substance may be added to the flow through the device to imitate common methods of use or treatment such as smoking of a cigarette, a cigar, a pipe or a *cannabis* cigarette. Optionally the device is fashioned to externally resemble the item used in such common uses.

In some embodiments, at least one sensor 314 is positioned at a location suitable for assessing one or more parameters of the flow that passes through the drug repository 310, for example within chamber 302. In some embodiments, the sensor 314 is configured to measure one or more of: rate, pressure, velocity, volume of the flow, or another direct or indirect indication of flow rate. Optionally, the flow estimation takes into consideration a fixed volume of the chamber. In some embodiments, the sensor is positioned at a location in which it is less prone to damage and/or less prone to any physical, chemical or mechanical phenomena that may affect the sensor's performance. For example, in a device in which a vaporization process takes place, the sensor may be positioned away from fumes, which may impede sensitivity and/or shorten the sensor's life. Optionally, sensor 314 is positioned distal to an opening 306 which is a proximal opening of conduit 300, and proximal to a drug repository 310. A potential advantage of this position is to allow sensing of pressure changes at a position where change in pressure can be related to flow rate and/or total flow volume.

In some embodiments, chamber 302 comprises a distal opening 316 through which air enters, optionally in response to suction produced by inhalation of the user. Additionally or alternatively, in some embodiments, a pressure source schematically shown as a fan 312 is positioned at or near distal opening 316 to actively force air into the chamber. In some embodiments, a macro filter 318 extends across the opening, to reduce or prevent debris and/or other contaminating material from entering the chamber. In some embodiments, fan 312 is activated (for example by a controller 313) in response to an indication from sensor 314, such as an indication of inhalation flow rate that is lower than a threshold needed to activate drug substance release.

In some embodiments, a shunting conduit 320 joins conduit 300 at a location which is more proximal to the user than a location in which flow through chamber 302 passes through the drug repository. Optionally, shunting conduit 320 joins conduit 300 at a location which is close to a location in which flow through chamber 302 passes through the drug repository. In some embodiments, ambient flow into conduit 300 through shunting conduit 320 is controlled by one or more valves 322 that optionally act as shunt valves.

In some embodiments, ambient flow entering the device is delivered through a bypass conduit 324 without being restricted by drag of the drug conduit 300. In some embodiments, ambient flow through conduit 324 is controlled by one or more bypass valves 326. Optionally, the effective cross-section (e.g. the opening) of bypass conduit 324 is larger than that of drug conduit 300 (e.g. proximal opening 306). The combined effective cross sections of bypass conduit 324 and drug conduit 300 affect the flow rate through opening 308 of mouthpiece 304. Accordingly, the effective cross section of drug conduit 300 is for example at least 2 times smaller, at least 3 times smaller, at least 5 times smaller or intermediate, larger or smaller values. Additionally or alternatively, the summed cross-sectional area of the proximal openings of the bypass conduit 324 and the drug conduit 300 is at least 25% larger than the proximal opening(s) of the drug conduit 300 alone, at least 50% larger, at least 100% larger, at least 200% larger, or larger by another greater, smaller, or intermediate factor.

In an embodiment, opening 306 has a diameter of 3 mm, and the opening of bypass conduit 324 has a diameter of 8 mm.

It is noted that entry and/or passing of flow such as ambient flow is provided, in some embodiments, by a coupling other than a junction between two or more conduits. In an example, ambient air flow to the drug conduit and/or ambient air flow joining the already combined flow is provided via pores and/or other openings in the drug conduit, such as pores along the walls of the conduit. In some embodiments, an intersection between the conduits comprises a porous membrane. Optionally, a flow regulator such as a valve is positioned at a location suitable to control an array of pores, for example allow flow through some pores and obstructing or partially obstructing flow through others. Such mechanism may contribute to producing a "sleeve like effect", for example as described herein.

In an example of a flow regime, ambient air (marked by the white arrows) enters chamber 302 through filter 318. The air flows through drug repository 310. Drug substance-infused air, marked by the black arrows, flows from chamber 302 and into conduit 300. At a location along conduit 300 more proximal to the user, ambient air may be permitted to flow into conduit 300 through shunting conduit 320. Entry of ambient air through shunting conduit 320 and/or the rate of ambient air flow through shunting conduit 320 may be controlled by shunt valve 322, for example based on an indication of flow rate through the drug dose as provided by a flow rate sensor 314. Optionally, the drug substance-infused air (depicted as a black arrow) mixes or combines with the ambient air that entered through shunting conduit 320, and the combined flow (marked by the gray arrows) continues to flow through conduit 300 until exiting through opening 306 and into the mouth and lungs of the user.

In some embodiments, bypass valve 326 is opened to allow general ambient air (shown as a white arrow) into the device through bypass conduit 324, wherein the allowed airflow comprises a bypass airflow. Optionally, the ambient flow enters mouthpiece 304 and exits it through opening 308. Optionally, flow through the conduit 300 and/or shunting conduit 320 is reduced or terminated. Optionally, the reduction or termination of flow through the other conduits and/or the relatively large opening 308 of mouthpiece 304 through which the ambient air exits the device contribute to the reduction of drag forces, potentially facilitating the user's inhalation through the device and enabling a large volume of air to pass through to the user within a short period of time. In some embodiments, the shunting conduit 320 and the drug conduit 300 are kept separate up to the proximal aperture of the mouthpiece. Optionally, the two conduits are completely separate, including separate mouthpiece apertures; however, it is a potential advantage to merge the two airflows earlier (e.g. at a distal region of the mouthpiece), to avoid the possibility that one airflow would become selectively blocked by the user's own mouth parts.

In some embodiments, out of the total volume of air that passes through the inhaler device to the user during a use session, about 5%-20%, 10%-50%, 30%-70% or intermediate, higher or lower ranges pass through the drug dose.

In some embodiments of the invention, at least one temperature sensor 315 is provided at a location allowing it to estimate and/or measure temperature at a dose cartridge (drug repository) 310. Optionally, the measurement is made continuously, or at one or more discrete times during a drug substance administration regime where heat is used to extract the drug substance. Optionally, temperature distribution is measured among two or more regions of the dose cartridge. Optionally temperature is measured without contacting the drug dose and without interfering with airflow therethrough, for example by infrared (IR) sensing. Said sensor 315 may be positioned in the area before the carrier airflow meets the drug cartridge. Where sensor 315 is an optical sensor (such as an IR sensor), it is optionally configured, for example, to take readings from a field of view 315A of the dose cartridge 310. Potentially, use of an IR sensor positioned away from the drug dose itself reduces sensor degradation due, for example, to vapor condensation and degradation of the sensitivity of sensor 315.

In some embodiments, a controller (not shown) receives the temperature data to provide control of heating according to a planned heating profile and/or as a feedback parameter indicating airflow. For example, heating is provided until a target temperature is reached, heating amount is modulated based on a rate at which target temperature is being approached, and/or heating amount is modulated to maintain a target temperature in a targeted range. This is a potential advantage, for example to reduce variability caused by changes in available heating power, differences in manufacturing, and/or differences in environmental conditions (e.g., ambient temperature and/or humidity).

In some embodiments, a controller uses received temperature data to estimate an amount of drug substance vaporized. Optionally, this also comprises an estimate of the amount of drug substance actually received by the inhaler. Optionally, this estimate is used for example, in process monitoring, and/or in planning the timing/dosage in the next inhalation as a part of a regimen.

In some embodiments, temperature data is used with feedback control of a flow pattern. For example, the combined effect of air flow and temperature define the amount of drug substance vaporized within a given period. The measure of one of both the two is optionally used in real time (i.e., during the same inhalation) to control the other and/or the operation of the system overall. For example, underheating of the drug dose (potentially influenced by cooling from the carrier airflow) is optionally counteracted at least in part by reducing the fraction of flow which passes through the drug dose and/or increasing a heating period. Additionally or alternatively, if high flow is detected, heat output is raised so that the extraction temperature remains within specified parameters. Similarly, over-heating/under flow are potentially addressed by one or both of lowering heating energy and/or increasing the fraction of total air flow which passes through the drug dose and/or adjusting a time period allotted for drug substance extraction or a portion thereof. It is a potential advantage to have both types of information, since the cooling effects of air flow are potentially variable, depending, for example, on humidity and/or air pressure; while temperature measurements alone do not necessarily establish that a drug substance is being delivered as intended.

Reference is now made to FIGS. 4A-4E, which illustrate flow regulation at various time points following an indication of inhalation, according to some embodiments of the invention.

The following illustrations describe flow regulation in an inhaler device in which drug substance is released over a certain time period, in this example over a time period of 2.9 seconds. In some embodiments the drug substance release time may vary (depending, for example, on the type of drug dose, drug substance to be released, and/or the dose administered to the user). Also, in some embodiments the drug substance release time is not predefined, and is dynamically adjusted during use, for example based on inhalation parameters of the user.

In some embodiments, drug substance release is activated in response to a trigger, for example a detected inhalation flow rate above a certain threshold. Additionally or alternatively, the trigger comprises mechanical activation (e.g. by pressing a push button) or sensing contact with the mouthpiece. Optionally, sensing a flow of air exhaled by the user into the device is used to trigger the activation of drug substance release, for example by sensing a flow above a specific threshold. Optionally, by sensing a parameter of this exhalation (e.g. a pressure change, a rate of pressure change and/or a flow rate within the device) the user's inhalation capacity may be estimated. Such estimate may be used to control one or more of the parameters of operation of the device, including for example, the duration of any part of the flow profile, the timing and temperature of heating, a duration and/or timing of obstructing flow through the device, etc.

Figure 4A:
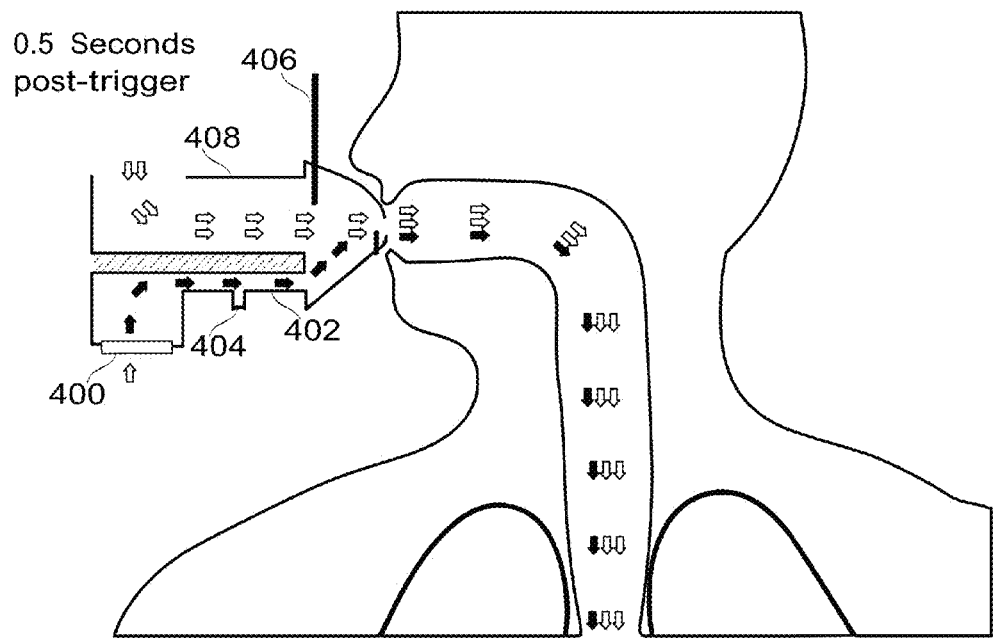
FIGS. 4A-4E illustrate flow regulation at some time points following an indication of inhalation, according to some embodiments.

In FIG. 4A, illustrating flow through the device at 0.5 seconds post activation of drug substance release, air (indicated by the white arrows) flows into drug repository 400, and passes through it carrying the drug substance into drug conduit 402 (now indicated by the black arrows). In some embodiments, a sensor 404 configured along drug conduit 402 senses the flow rate. Optionally, based on the indication from the sensor, valve 406 is moved to a position in which ambient flow through shunting conduit 408 is allowed. In some embodiments, valve 406 comprises a plurality of partially open configurations in which a certain rate and/or volume of flow is allowed into the device, so that flow in excess of the target flow through the drug dose (as indicated, for example, by sensor 404) will be obtained from the atmosphere via shunting conduit 408. Optionally, valve 406 is mechanically configured so that flow in excess of the target flow through the drug dose, as perceived by the valve itself, will be obtained via shunting conduit 408 without need for sensing.

In an example, the target flow comprises a constant rate of flow through the drug dose, of 1 L/min for example. If the user inhales at rate of 3 L/min, valve 406 will open to allow flow at a rate of 2 L/min through shunting conduit 408.

Figure 4B:
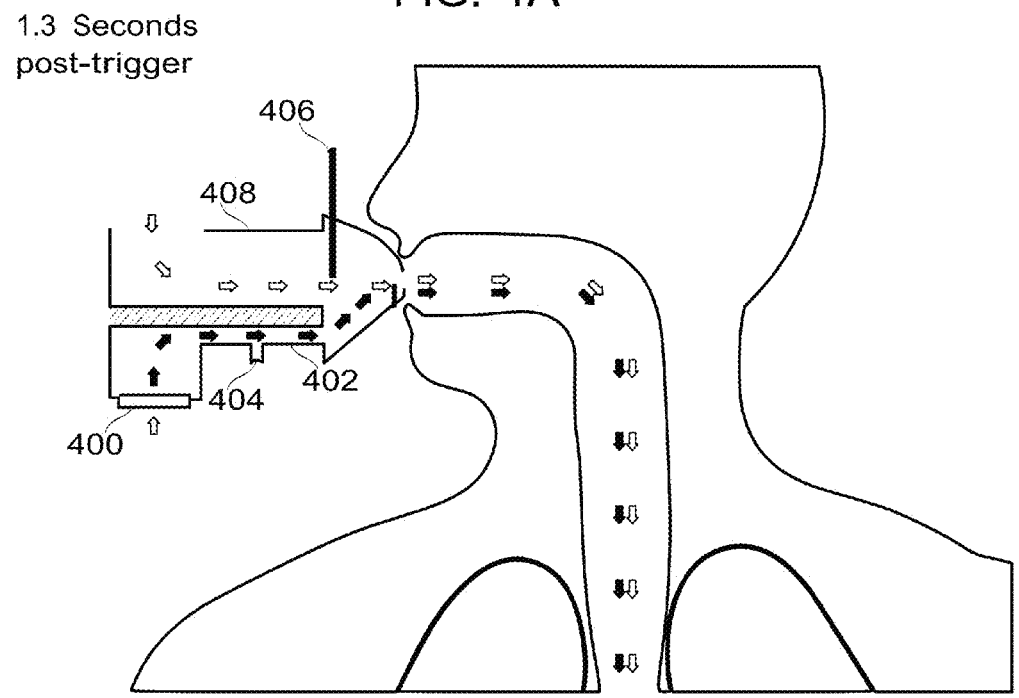

In FIG. 4B, illustrating flow through the device at, for example, 1.3 seconds post activation of drug substance release, a change in flow rate through the drug dose may be observed by sensor 404 and/or perceived by a mechanical valve 406. In an example, if the flow rate is lower than a target rate of flow through the drug dose, the positioning of valve 406 is dynamically adjusted to obtain less flow from the atmosphere, thereby increasing the upcoming flow through the drug dose. In the example described above, if at this point the user inhales at a rate of 2 L/min, a rate of 1 L/min will be allowed through shunting conduit 408, maintaining the target, constant flow rate of 1 L/min through the drug dose.

Figure 4C:
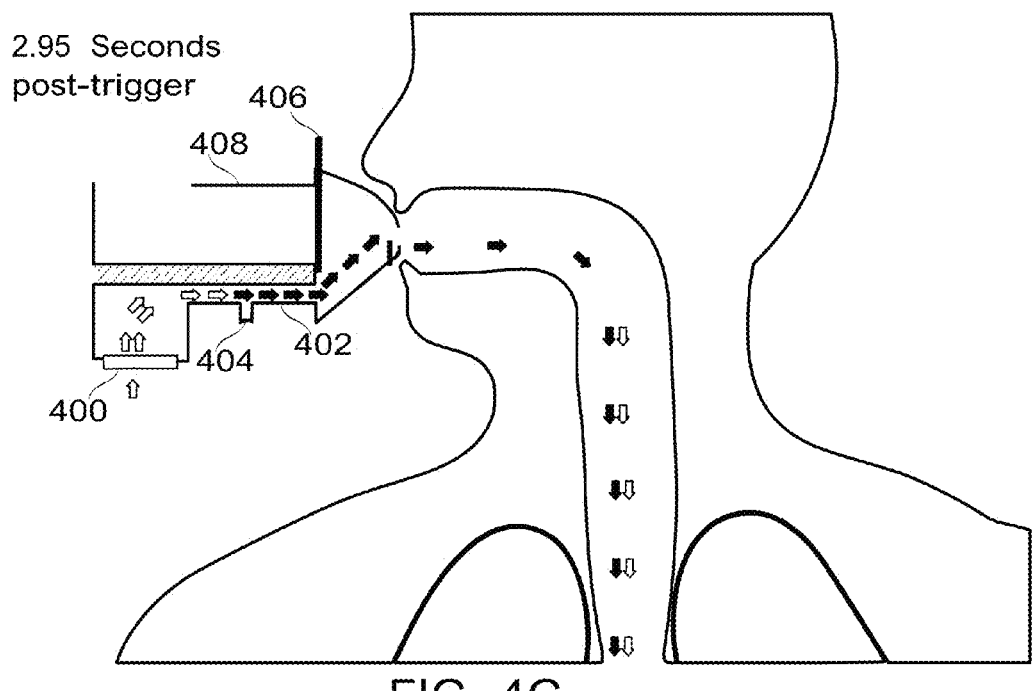

In FIG. 4C, illustrating flow through the device at 2.95 seconds after activation of drug substance release (therefore 50 msec after drug substance release was terminated), valve 406 is moved to a position in which shunting conduit 408 is fully obstructed, causing all flow that enters the device (for example in response to suction caused by inhalation of the user) to pass through drug conduit 402, flushing away drug dose residue.

Figure 4D:
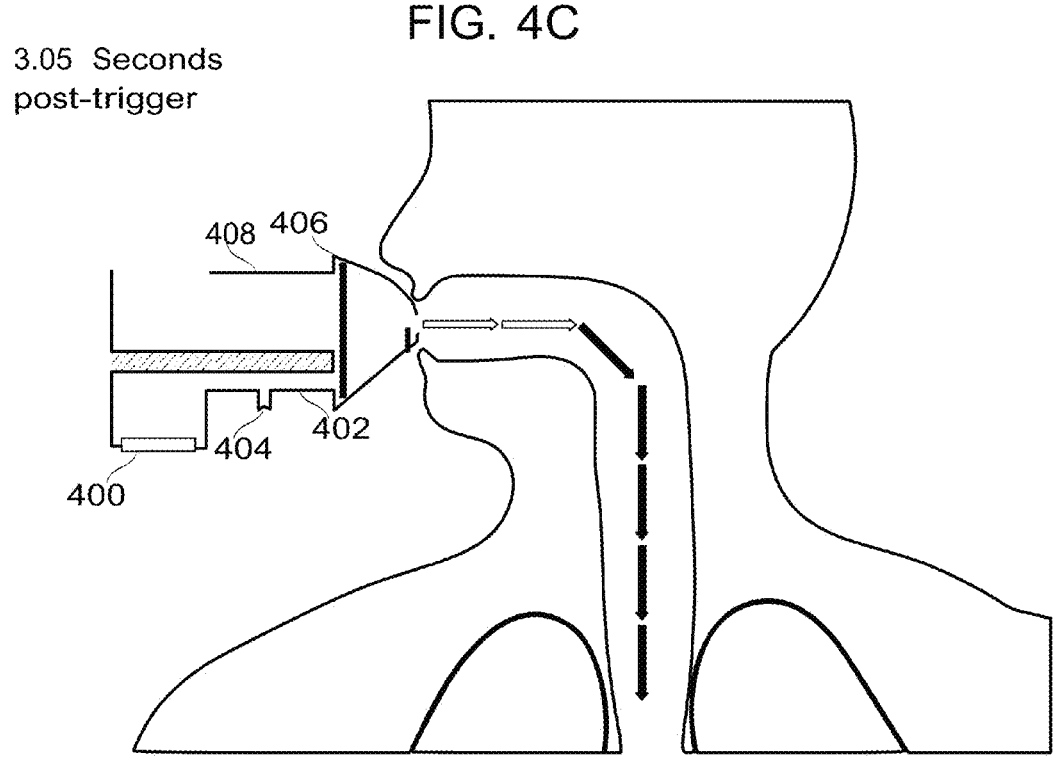

In FIG. 4D, at 3.05 seconds post activation of drug substance release, optionally all flow to the user is obstructed. In some embodiments, the full obstruction is performed for a predefined time period, for example between 5 and 400 msec, or for a greater, smaller, or intermediate period. Additionally or alternatively, the duration of obstruction is dynamically selected and/or adjusted, for example during use, for example based on the inhalation parameters of the user. In some cases, obstruction of flow evokes a sensory stimulus in the user's body, which may involve excitatory response of the respiratory muscles.

Figure 4E:
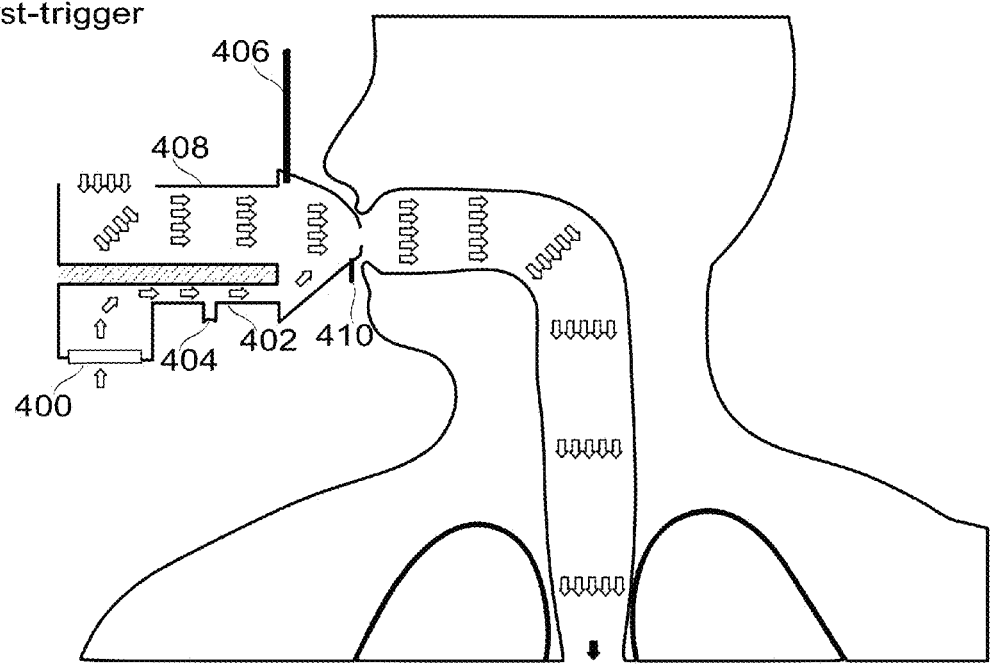

In FIG. 4E, at 3.11 seconds post activation of drug substance release, valve 406 fully opens to allow flow through conduit 402 and through shunting conduit 408. Optionally, an additional valve 410 configured at mouthpiece 412 opens to increase a cross sectional area of a passage through mouthpiece 412, thereby allowing increased flow rate through the mouthpiece.

In some embodiments, the sudden rise in flow rate provides an indication to the user. Additionally or alternatively, the operational sequence including relatively resisted flow (resisted due to drag forces), followed by a reduction or obstruction of flow, followed by increased flow at relatively low resistance provides an indication to the user. Optionally, the indication notifies the user regarding the use or treatment status, for example signaling the user to cease inhalation and optionally remove the inhaler from the mouth. In some embodiments, an indication for example as described (or one including one or more of the operational actions, for example a sudden obstruction of flow) is provided during use or treatment at a time point other than the end of the use, for example to signal the user to breath more deeply.

A potential advantage of an operation sequence comprising a substantial reduction or obstruction of flow, followed by a rapid rise in the flow rate and/or volume may include triggering of respiratory reflexes that may reduce an anatomical "dead space" effect, and stimulate deep lung inhalation. Another potential advantage of an operation sequence in which a direct lung-device interface is obtained may include increasing the user's compliance and reducing the need for a cognitive effort to be made by the user, as compared to devices in which only audible and/or visible and/or tactile indications are provided.

It is noted that the flow regulation regime and time schedule described hereinabove in FIGS. 4A-4E is potentially advantageous in a device in which drug substance release comprises extraction of one or more active substances by heating the drug dose. For example, 1,500 μg of active ingredient are extracted from a 15,000 μg source drug dose material, and are provided over a use session of approximately 3 seconds. In another example, 500 μg of active ingredient are extracted from a 15,000 μg source drug dose material, and are provided over a use session of approximately 1.5 seconds.

Optionally, a target heating profile and/or a target airflow profile includes fluctuating operation during the drug substance extraction. As shown, for example, in FIGS. 4A-4E, the drug substance is optionally delivered during a heating period of 2.9 seconds. During this period, drug substance-infused vapors are optionally dynamically mixed with ambient air; for example at an average ratio of about 80% air:20% drug substance-infused air. Optionally, this period is followed by a period (e.g., about 0.1 seconds) during which 100% of airflow is through the drug dose; and thereafter a brief period in which airflow is at least partially blocked (e.g. for less than 100 msec) may take place. Finally, flow is optionally resumed for a period in which 100% ambient air is provided (even if partially passing through a cold and potentially depleted dose cartridge).

This flow pattern may be depicted schematically as follows (without detailing the blocking period):

(A80%, D20%) for 2.9 seconds, then D100% 100 ms, then A100% 900 ms where A=Air (air substantially free of drug substance) and D=Drug (carrier airflow carrying drug substance).

In some alternative embodiments, a different protocol may be used, where the portion of carrier airflow to ambient airflow is controlled variably such that the concentration of drug substance received by a user varies during extraction. For example:

[(A70%, D30%) for 200 ms, (A95%, D5%) for 200 ms], repeat until 2.9 seconds are up, then D100% 100 ms, then A100% 900 ms or:

[(D100%) for 50 ms, (A100%) for 100 ms], repeat until 2.9 seconds are up, then D100% for 50 ms, D100% 100 ms, then A100% 900 ms or another protocol using different ratios of A and D flow, greater, smaller, or intermediate period lengths, and/or greater, smaller, or intermediate numbers of period repetitions.

Figure 5:
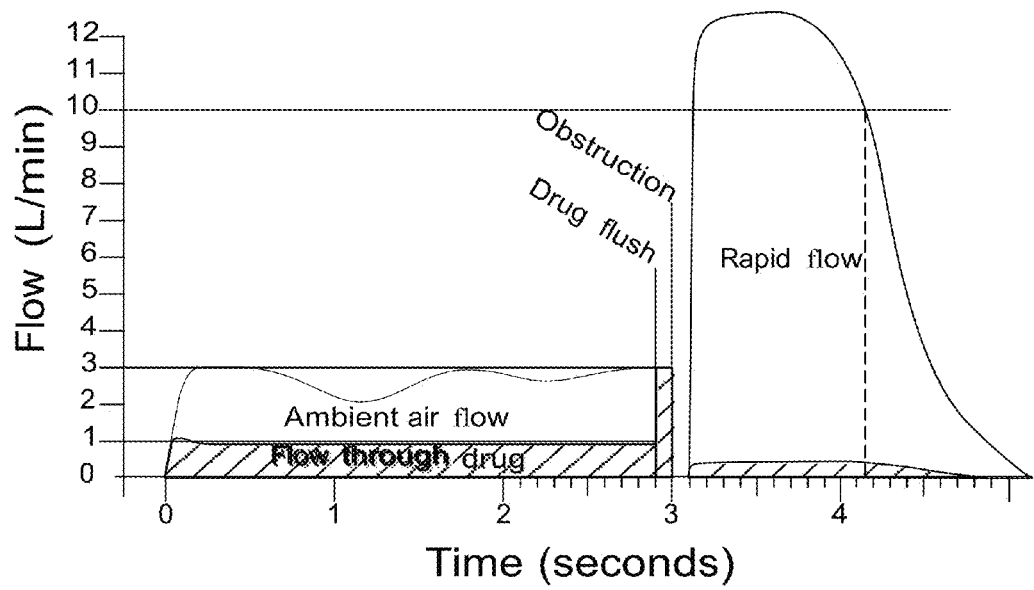
FIG. 5 is a schematic graph of a flow regime for pulmonary delivery of a drug substance, according to some embodiments.

Reference is now made to FIG. 5, which is a schematic graph of a flow regime for pulmonary delivery of at least one active drug substance, according to some embodiments of the invention, as also shown, for example, in FIGS. 4A-4E.

In the flow graph shown herein, an example for a use session over a total duration of approximately 4-5 seconds is described. It is noted that use sessions in accordance with some embodiments may include a different duration, a different target flow profile through the drug dose, a different air pulse volume, a different drug substance release period, and/or other parameters that are different than the parameters described herein.

During the first 2.9 seconds, drug substance is released. The target flow profile through the drug dose comprises a constant flow rate, in this example of 1 L/min. A rate of ambient air flow through the inhaler fluctuates between various values, optionally in response to a dynamically changing inhalation flow rate of the user. At 2.9 seconds, ambient flow is restricted, and in the shown example flow rate through the drug dose increases, potentially flushing drug dose residue. At 3 seconds, a full obstruction of flow into the device occurs, followed at 3.1 seconds by a pulse of air at a high flow rate.

In some embodiments, a targeted total volume of the air pulse and/or a duration over which the pulse is supplied to the user are selected to reduce or eliminate an effect of the anatomical dead space (a portion of the human airways in which gas exchange does not take place). In an adult human, the anatomic dead space is about 150 ml in volume. Accordingly, in the flow regime shown herein, an air pulse at a flow rate higher than 10 L/min is provided over a duration of about 1 second, providing a total of about 166 ml, which is a volume larger than the anatomical dead space, potentially chasing the drug substance-infused air previously inhaled by the user deeper into the lungs.

In an example of a user inhaling at an average flow rate of 5 L/min, and assuming a constant target flow rate through the drug dose of 1 L/min, during at least 70%, 80%, 90% or intermediate, higher or lower percentages of a total duration of the use session the ambient flow rate will be higher than the flow rate through the drug dose. Various consequences of supplying the user with ambient air flow at a rate higher than a rate of drug substance-infused flow may include producing a deeper inhalation. A potential advantage of a deeper inhalation may include reducing an amount of drug substance that is exhaled by the user. Optionally, in such a case, more drug substance is absorbed in the lungs. Optionally, less drug substance is released to environment.

Optionally, a time period in which the flow rate of drug substance-infused air to the user may be higher than the flow rate of ambient air to the user includes the time period in which ambient flow is obstructed to cause flushing of the drug substance, and flow rate through the drug dose is increased.

Figure 6:
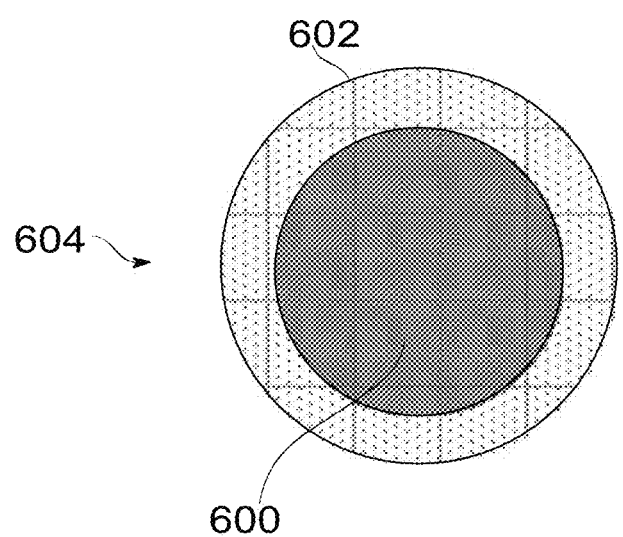
FIG. 6 is a schematic cross section of a flow regime through a conduit of an inhaler device configured for reducing adherence of drug dose residue to the inner walls of the conduit, according to some embodiments.
Figure 7:
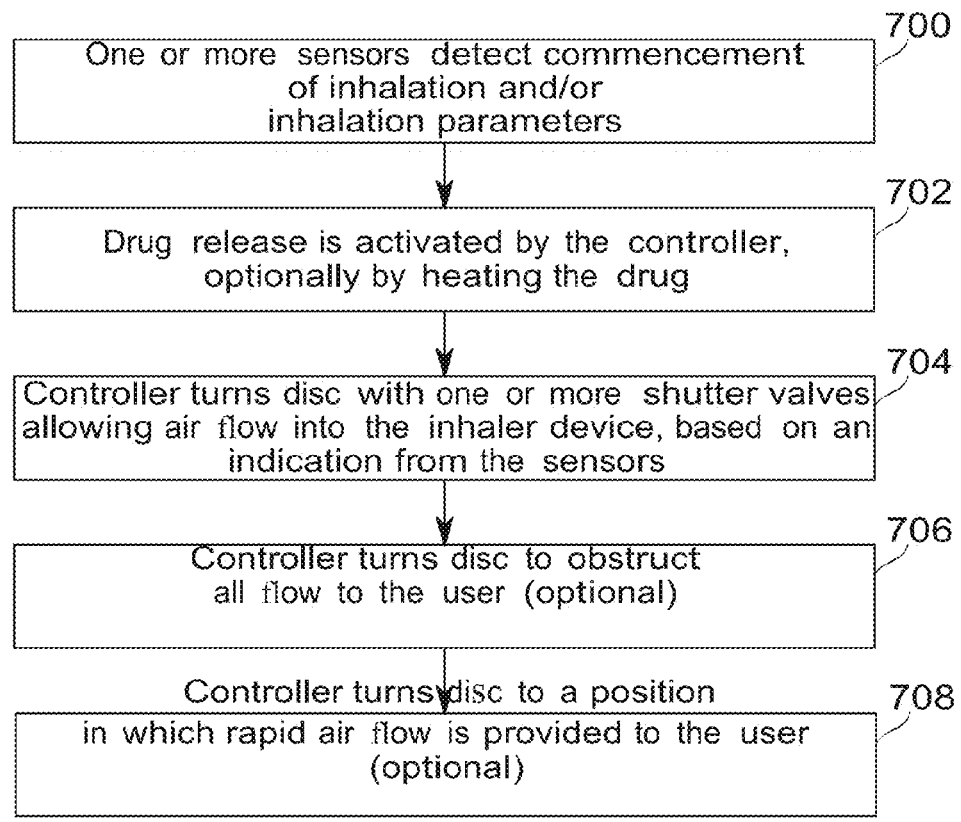
FIG. 7 is a flow chart of a mechanical operation of an inhaler device, according to some embodiments.

Reference is now made to FIG. 6, which is a schematic cross section showing an air flow regime in a conduit configured for reducing adherence of drug dose residue to the inner walls of the conduit, according to some embodiments of the invention.

In some embodiments, entry of ambient air flow into the drug conduit 604 (e.g. from a shunting conduit) produces a sleeve like effect within the drug conduit, in which flow 600 that is closer to a central longitudinal axis of the conduit comprises a drug substance concentration that is higher than a drug substance concentration in flow 602 along the circumference of the conduit. Optionally, the drug substance concentration decreases in a radially outward direction.

Optionally, obtaining the sleeve like effect includes controlling ambient air flow into conduit 604, such that ambient flow enters from a plurality of directions around the conduit 604, optionally at equal rates from all directions, such that the chance for turbulence is reduced or minimized.

A potential advantage of the sleeve-like effect may include reducing adherence of the drug dose and/or extracted drug substance(s) to the walls of the conduit. This may be especially advantageous when the administered drug substance(s) and/or products of the drug substance extraction process have a tendency to stick to the conduit walls. In an example, when the drug dose comprises plant material such as *cannabis* or *Papaver somniferum*, products of the extraction process (such as products of vaporization) may include oily and/or viscous substances, such as oily THC, opium latex and/or other substances which may adhere to the walls of the conduit. In some cases, adherence to the walls may result in the delivery of lesser amounts than the ones administered to the user. In some cases, materials may build up on the conduit walls and potentially interfere with the flow. In some cases, build up may affect the accuracy of flow rate measurement, for example if occurring at a location of the sensor. Optionally, the sleeve-like effect reduces one or more of the risks described herein.

In some embodiments, a sleeve-like effect takes place in other portions and/or components of the inhaler device, such as the mouthpiece. Optionally, a "double sleeve" effect takes place when ambient air flowing through a bypass conduit meets the combined flow. Optionally, the double sleeve effect is observed at and/or in proximity to the mouthpiece, optionally at the opening of the drug conduit near or within the mouthpiece.

Reference is now made to FIG. 7, which is a flow chart of a mechanical operation of an inhaler device, according to some embodiments of the invention.

In some embodiments, operation of an inhaler device to provide flow-controlled pulmonary delivery of a drug substance to a user is performed according to one or more of the steps described herein.

In some embodiments, inhalation and/or one or more parameters of inhalation are detected, including, for example, one or more of: flow rate, volume, velocity, pressure and/or other parameters, optionally by one or more sensors (block 700). Optionally one or more or all of the parameters are detected and/or are used to estimate one or more parameters of airflow near or through a dose cartridge.

In some embodiments, a controller receives input from the one or more sensors, and if the initial activation conditions are met (e.g. the inhalation flow rate is higher than a threshold), the controller activates drug substance release (block 702). Optionally, activation of drug substance release comprises heating a drug dose to release one or more drug substances; for example, by passing an electric current through an electrically resistive element in heating proximity to the dose cartridge or incorporated therein. Optionally, the resistive heating element is arranged to heat the drug dose without blocking airflow therethrough. For example, the resistive heating element allows airflow to enter and/or leave via at least 25% of the surface area of a face of the drug dose pallet, at least 33%, at least 50%, or via another larger, smaller, or intermediate relative surface area of a drug dose pallet face.

In an embodiment, heat is applied to plant material, for example *cannabis*, and air flow through the heated material evacuates one or more active substances such as THC from the *cannabis*. Optionally, the plant material is contained within a cage-like wire structure, which is heated to vaporize the active substances. In some embodiments, extraction parameters such as a temperature profile of the heated plant material, a duration of heating, an amount of plant material being heated and/or other parameters of extraction may affect flow through the drug dose. In some embodiments, when drug substance release involves heating of the drug dose, a rate of ambient air flow that diffuses with the flow that passed through the drug dose, such as ambient air entering through a shunting conduit, is selected and/or modified to be high enough to cool down the heated flow that passed through the drug dose, reducing a temperature of the flow before the flow reaches the user.

In some embodiments, based on an indication received from the sensors, the controller operates a regulating mechanism to provide controlled ambient flow into the device. In some embodiments, the regulating mechanism comprises a plurality of valves, which may be operated separately from each other and/or simultaneously. In some embodiments, a plurality of valves such as 2, 4, 6 or an intermediate, larger, or smaller number of shutter valves are configured on a rotatable disc shaped element, positioned in communication with one or more conduits such as the drug conduit, shunting conduit, and/or bypass conduit of the inhaler device. Optionally, the valves are holes in the rotatable disc, extending between proximal and distal faces of the disc. An example for such rotatable disc is described in further detail in connection with FIGS. 9A-9B and 10A-10C.

In some embodiments, the controller turns the disc element to allow flow of ambient air into the device (block 704), such as flow through the shunting conduit. Optionally, an extent of overlap between a valve opening and a conduit opening is adjusted by rotating the disc, to allow a targeted volume of flow to pass through the valve opening. Optionally, an arrangement of the valves on the disc is designed so that when a first valve is open (or partially open), one or more other valves or closed, or vice versa. Alternatively, arrangement of the valves is on two or more discs, optionally allowing separate control of the valves for each of at least one second conduit and at least one third conduit.

In some embodiments, the valves are arranged relative to each other and/or relative to the conduits they are in communication with to provide a full obstruction of the flow to the user, for example when the disc is rotated to a certain angular position (block 706).

In some embodiments, optionally following obstruction of flow, the controller turns the disc to a position in which a pulse of flow can be provided to the user (block 708), for example by fully opening valves that block the bypass conduit(s). Optionally, valves that block the drug conduit(s) and/or valves that block the shunting conduit(s) may be opened as well.

Figure 8:
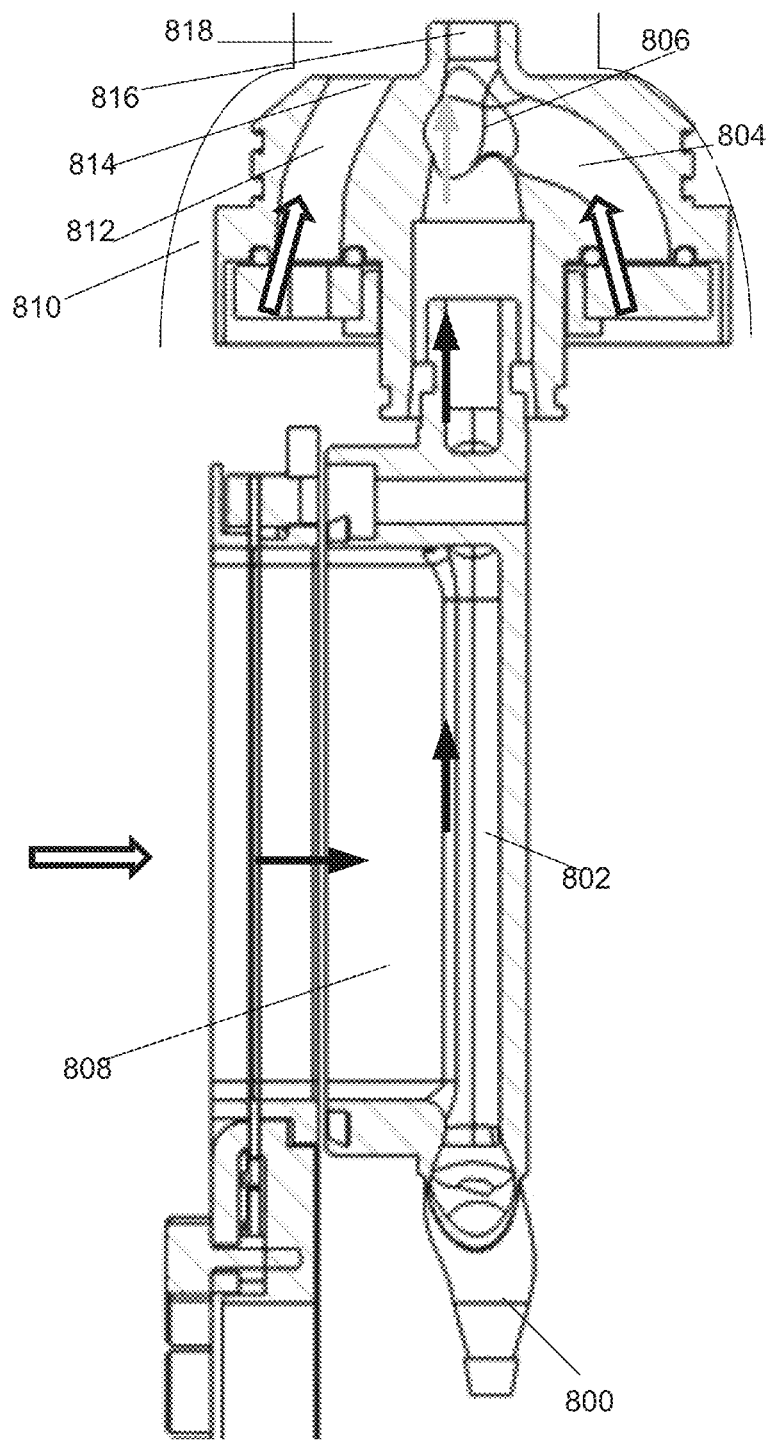
FIG. 8 illustrates a longitudinal cross section view of an inhaler device, according to some embodiments.

Reference is now made to FIG. 8, which illustrates a longitudinal cross section view of an inhaler device, according to some embodiments of the invention.

In FIG. 8, the white arrows indicate ambient air flow, the black arrows indicate flow through the drug dose, and the gray arrows indicate a combination of ambient flow that joined the flow that passed through the drug dose.

In the structure shown herein, a flow sensor 800 is positioned at a point along drug conduit 802, to sense the flow rate through the drug conduit. This point may be distal to the user. Optionally, the sensor can be configured at any point axially along drug conduit 802 which, along the flow path, located before (i.e. distal to) a first point in which shunting air is allowed to flow into the drug conduit, such as at a junction 806 between a shunting conduit 804 and the drug conduit. Optionally, junction 806 is positioned closer to a proximal opening 816 of drug conduit 802, such as within mouthpiece 810. A potential advantage of a junction between the shunting conduit and the drug conduit which is located at a relatively distal point along the drug conduit (i.e. farther away from the user end) may include reducing the amount of drug dose residue that adheres to the walls of the drug conduit.

In some embodiments, drug substance-infused air enters chamber 808, from which it enters drug conduit 802. Optionally, chamber 808 is a part of the drug conduit 802 (for example by the drug conduit widening in the distal direction and/or at a distal portion of it).

In some embodiments, constant movement of the drug substance-infused air through the chamber and into the drug conduit is maintained. A potential advantage of continuously moving flow may include reducing a risk of condensation of drug dose residues and/or the one or more released drug substances. Alternatively, at least some volume of drug substance-infused air is allowed to accumulate within the chamber, for example to cool it down before it enters the drug conduit and delivered to the user.

In some embodiments, one or more bypass conduits 812 allow for ambient air flow into the device. Optionally, an opening 814 of bypass conduit 812 is located adjacent opening 816 of drug conduit 802, both being proximal to the user. Optionally, both openings 814 and 816 lead to proximal opening 818 of mouthpiece 810. As previously referred to herein, when ambient flow through bypass conduit 812 is enabled, drag forces are reduced and a resistance the user encounters during inhalation decreases, for example as compared to a state in which only flow through drug conduit 802 was allowed.

Reference is now made to FIGS. 13A-13D, which schematically illustrate a valve apparatus 1300 comprising an outer tube 1302 having valve apertures 1314, 1316, which are rotatable with respect to conduit apertures 1310, 1312 of internal tube 1301, for a performing a sequence of conduit openings and closures, according to some embodiments of the invention In some embodiments, internal tube 1301 comprises one or more first junctions, each between a drug conduit 1320 and a respective shunting conduit 1330. In some embodiments, internal tube 1301 comprises one or more second junctions, each between the drug conduit 1320 and a respective bypass conduit 1340. Additionally or alternatively, in some embodiments, bypass conduit 1340 leads directly to a mouthpiece aperture, for example, the aperture having diameter 1341. The internal tube 1301 is positioned within external tube 1302. Apertures 1314, 1316 of external tube 1302 correspond to apertures 1310, 1312 of the internal tube 1301, leading into the shunting and bypass conduits 1330, 1340, respectively.

In some embodiments, both the internal and external tubes 1301, 1302 are positioned along a longitudinal axis defined by the drug conduit 1320 and extend between a dose unit held by a holder of the inhaler device and a mouthpiece. The direction of air flow through drug conduit 1320 is depicted by arrow 1325.

The flow of air into the shunting and bypass conduits is optionally controlled by the relative position of the apertures 1310 with respect to apertures 1314 (these apertures working together comprise a shunt valve for the shunt conduit 1330, in some embodiments); and/or apertures 1312 with respect to apertures 1316 (these apertures working together comprise a bypass valve for the bypass conduit 1340, in some embodiments). Control of relative position comprises, for example, rotating (for example, rotating by a motor under control of a controller) at least one of the tubes 1301, 1302 around the longitudinal axis, and/or adjusting the relative positions of the tubes 1301, 1302 along the longitudinal axis (for example, by a motor under control of a controller). Optionally, two external (or internal) tubes are provided potentially allowing separate control of air flow into the shunting and bypass conduits. Optionally, any or all of the apertures and conduits 1310, 1312, 1314, 1314, 1330, 1340 are provided in sets, for example sets of two, three (illustrated in FIGS. 13A-13D), four or more for each element.

In some embodiments, valve apertures 1314, 1316 are positionable relative to conduit apertures 1310, 1312 (respectively) to open and close (or partially close/open) air flow into the conduits 1330, 1340. Optionally, the relative positionings and movements of apertures is such that when the shunting conduits 1330 are at least partially open, flow through the bypass conduits 1340 is blocked. Contrariwise, in some embodiments, opening the bypass conduits 1340 closes the shunting conduits 1330. Alternatively, complete opening of one valve accompanies complete closure of the other, with partial closure/opening of each valve during transitional positions.

In some embodiments, the bypass conduit valve apertures 1316 are on one external tube and the shunting conduit valve apertures 1314 are on another external tube. This potentially allows, for example, opening the shunting and bypass conduits independently one from the other, in addition to the positions afforded by the example shown in FIGS. 13A-13D.

In some embodiments, any or all of the "all conduits at least partially open", "only a portion of the conduits at least partially open" and "all conduits closed" alternatives are achieved by another arrangement. For example, rotational movement at one relative longitudinal position of the two tubes opens only one set of valves at a time, and relative longitudinal translation of the tubes at least partially opens (optionally, opens or closes) both sets of valves at once.

Figures 13A, 13B:
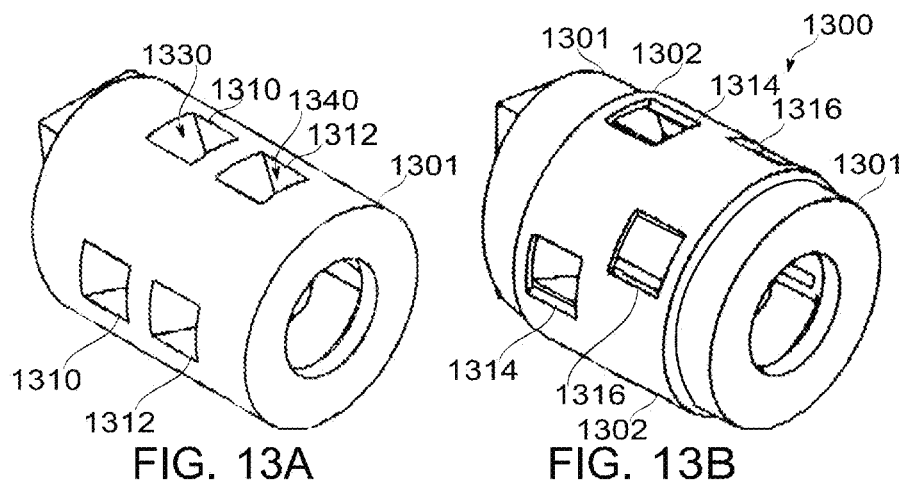
FIGS. 13A-13D schematically illustrate a valve apparatus comprising an outer tube having valve apertures, rotatable with respect to conduit apertures, of an internal tube, for a performing a sequence of conduit openings and closures, according to some embodiments.
Figure 13C:
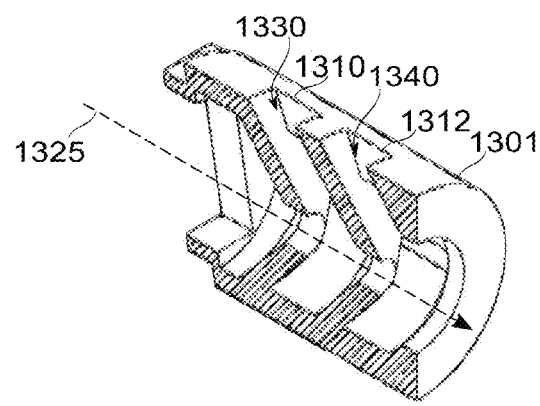
Figure 13D:
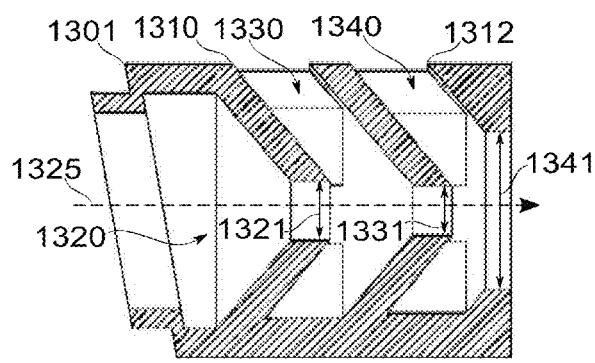

FIGS. 13C-13D show cross sectional views taken along a longitudinal axis of FIG. 13A, illustrating inner portions of conduits 1330, 1340 in communication with drug conduit 1320.

Flow from the shunting conduits 1330 joins flow in the drug conduit 1320 before a second aperture having a second diameter 1331 (and optionally joins after a first aperture having a first diameter 1321). Optionally, flow from the bypass conduits 1340 joins before a third aperture having a third diameter 1341. Additionally or alternatively, at least for a portion of an inhalation event, flow from the bypass conduits 1340 is kept separate from the drug conduit flow; for example, operated separately, and/or spatially separated. Optionally separation is by a partition extending to the mouthpiece, or by arranging flow so that a laminar effect is created substantially without mixing. Optionally, the second diameter 1331 is small enough to limit air flow via the device when the bypass conduits 1340 are closed. Potentially, this encourages a user to inhale with force.

Optionally, the third diameter 1341 is significantly larger than the second diameter 1331. Thus, when air is allowed to flow through the bypass conduits 1340, it does not experience the drag applied by the second aperture but rather flows relatively freely into the lungs.

Figure 9A:
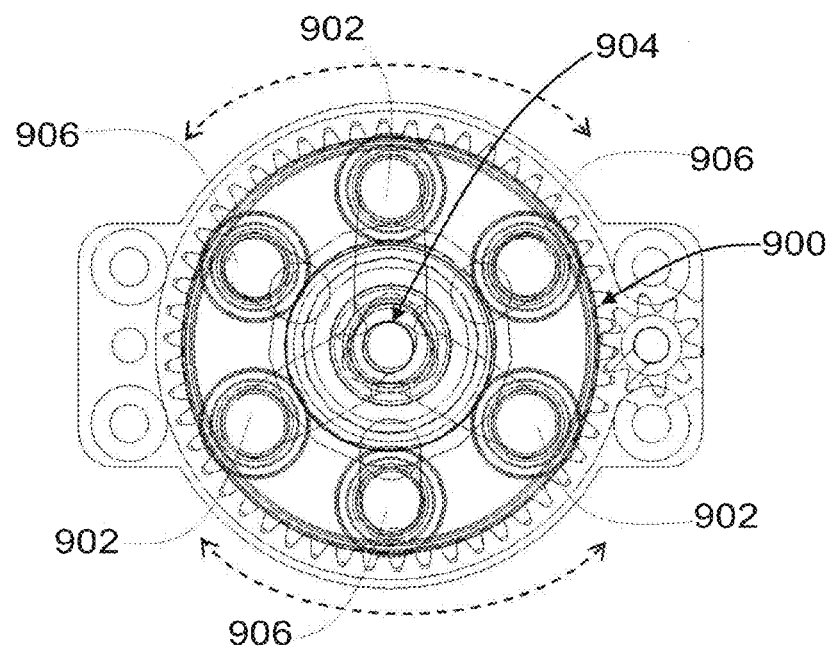
FIGS. 9A-9B are a front view cross section of a mouthpiece of an inhaler device (FIG. 9A) and a longitudinal cross section of the mouthpiece (FIG. 9B), according to some embodiments.
Figure 9B:
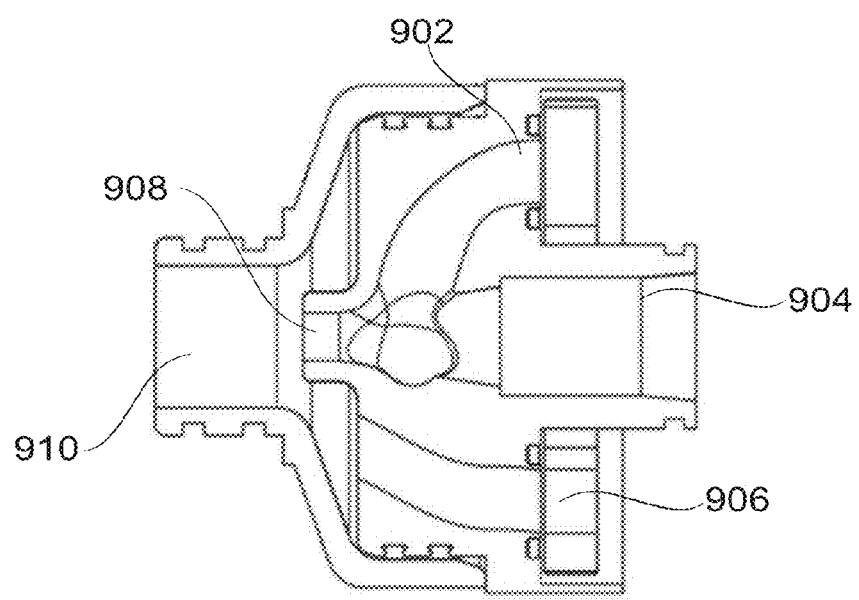

Reference is now made to FIGS. 9A-9B, which are a front view cross section of a mouthpiece of an inhaler device (FIG. 9A) and a longitudinal cross section of the mouthpiece (FIG. 9B), according to some embodiments of the invention.

In the cross section of FIG. 9A, rotatable disc 900 is turned to a position in which all conduits of the inhaler device are open to allow flow through, as all valve openings in disc 900 overlap with the distal openings of the conduits, through which air flow is allowed into the conduits.

Additionally or alternatively, in some embodiments, a valve may be positioned at a proximal end of a conduit. Optionally, a first valve is configured at a distal opening of a conduit, and a second valve is configured at a proximal end of a conduit, the valves operated respectively to provide a local regulation of flow through the conduit. Additionally or alternatively, a valve may be positioned at any point along a conduit.

The structure shown herein comprises three shunting conduits 902 (alternatively referred to as a single shunting conduit comprising three tracts), connected to a drug conduit 904 (a proximal opening of which is shown), and three bypass conduits 906 (alternatively referred to as a single bypass conduit comprising three tracts), extending to a proximal opening of the mouthpiece.

In some embodiments, disc 900 is a cogwheel that can be rotated by a motor, optionally in response to a signal received from the controller. In the configuration described herein, rotation of disc 900 simultaneously changes the relative positioning for at least a part of the valve openings on the disc, for example openings allowing flow through the shunting conduit(s)/tract(s). Optionally, the valve openings are arranged so that all conduits of a certain function (e.g. shunting conduits) are opened and/or closed at the same time. A potential advantage of adjusting all valve openings by a single movement may include simplifying the mechanical operation of the device, reducing the need for complex control over the valves, and/or reducing the need for small components, thereby potentially reducing a risk of device failure and/or potentially reducing its cost of manufacture. Alternatively, in some embodiments, one or more valves are operable independently of other valves.

In some embodiments, disc 900 is aligned with respect to drug conduit 904. Optionally, the rotation axis of disc 900 are parallel to (or, in some embodiments, united with) a longitudinal axis of drug conduit 904.

In some embodiments, the valve openings of disc 900 are symmetrically arranged with respect to drug conduit 904, for example with respect to a proximal opening of the drug conduit. Alternatively, an arrangement of the valve openings is asymmetrical.

A longitudinal cross section of the mouthpiece of FIG. 9A is illustrated in FIG. 9B. The proximal opening 908 of drug conduit 904 is shown to be positioned a distance away from a full opening 910 of the mouthpiece, for example to enable parallel flow of the ambient air that enters through bypass conduit 906, at least during some stages of operation of the device.

Figure 15:
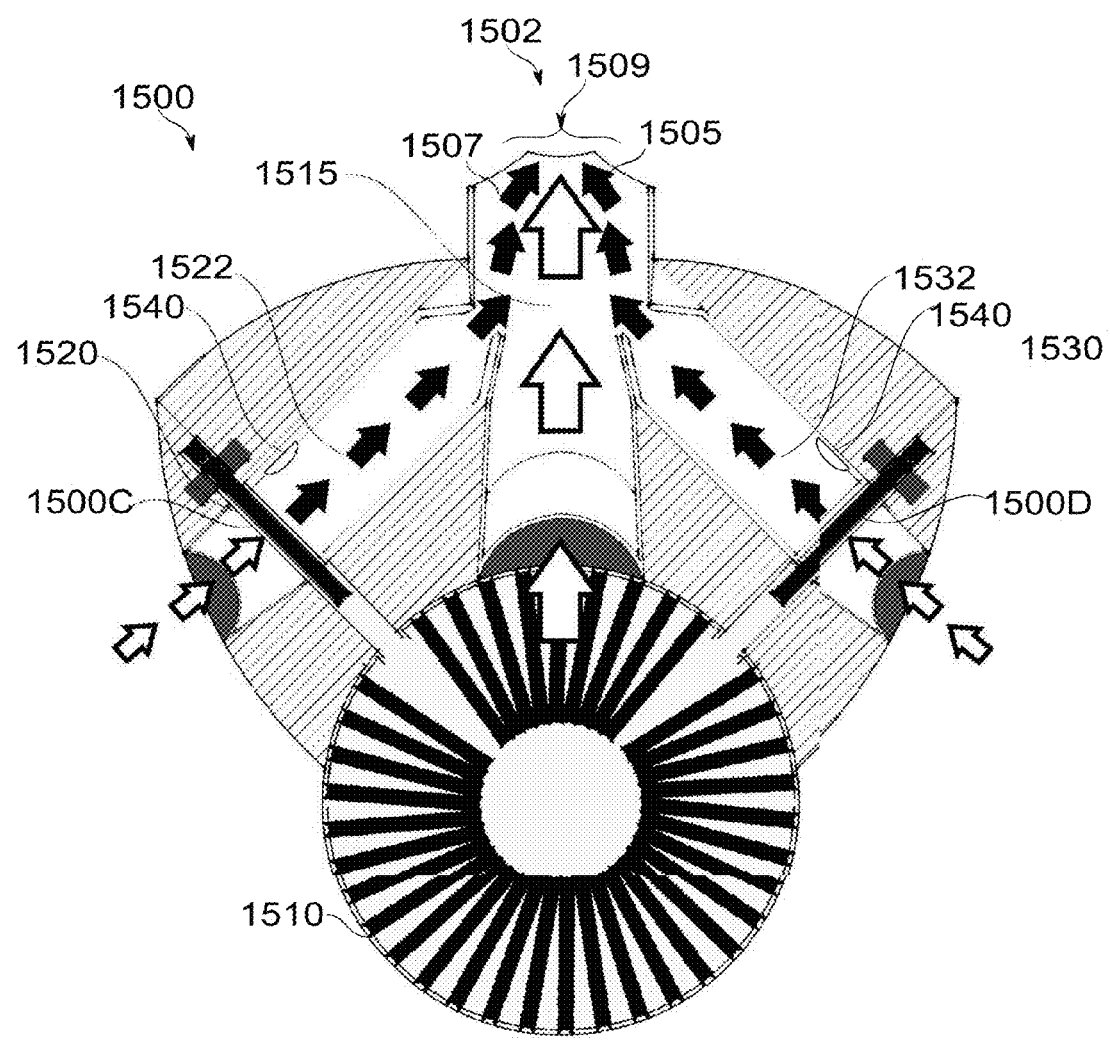
FIG. 15 schematically illustrates an inhaler for simultaneous administration of substances from a plurality of chambers in a corresponding plurality of carrier airflow conduit tracts, according to some embodiments.

Reference is now made to FIG. 15, which schematically illustrates an inhaler 1500 for optionally simultaneous administration of substances from a plurality of dose cartridge chambers 1520, 1530 in a corresponding plurality of drug conduits 1522, 1532, according to some embodiments. Inhaler 1500 comprises a carousel type magazine 1510 for storing a plurality of dose cartridges before and/or after use.

In some embodiments, a plurality of separate drug conduits 1522, 1532 are provided, each comprising a dose cartridge chamber (holder) 1520, 1530. In some embodiments, a dose cartridge chamber defines a cartridge position in a carrier airflow of a drug conduit by where it positions a dose cartridge when a dose cartridge is in the cartridge chamber, prepared for inhalation. Optionally, dose cartridges 1500C, 1500D are drawn from a single carousel-type magazine 1510 or other cartridge magazine. Alternatively, a plurality of magazines is provided. Cartridge drawing is optionally simultaneous, sequential and/or separately operated altogether, and optionally while the cartridge magazine(s) remain in a single position, or with movement of the magazine 1510 (e.g. rotation) between draws.

In some embodiments, flow through the drug conduits 1522, 1532 is at least partially regulated by providing a shunt conduit 1515 in flow communication with the drug conduits 1522, 1532. The total flow of air 1509 through the device due to inhalation from a mouthpiece 1502 is optionally divided among all conduits (for example by the sizing and/or size adjustment of conduit diameters and/or valves), such that the portion of airflow through each drug conduit 1522, 1532 is adjusted to be within a targeted carrier airflow profile. Remaining airflow is optionally directed through the shunt conduit 1515. Optionally, the drug conduits are operated separately (for example, only one is operated, or both are operated in sequence).

Optionally, sensors 1540 providing data (e.g. airflow and/or temperature data indicative of airflow and/or temperature at the dose cartridges during operation) for control are optionally positioned near or via one or more of the dose cartridges 1500C, 1500D. Control optionally comprises adjustment of airflow (for example, by adjustment of a valve or aperture position) such that both dose cartridges 1500C, 1500D simultaneously experience airflow 1505, 1507 within a given range. Alternatively, adjustment is such that a part of the airflow sequence is controlled with respect to a first chamber 1520, while another part is controlled according to second chamber 1530. Optionally, in some sessions, only one of chambers 1520, 1530 is used.

In some embodiments, a plurality of tracts for shunting conduit 1515 is provided, for example, one in separate association with each of the drug conduits 1522, 1532. Optionally, the air flowing in each of the drug conduits 1522, 1532 is combined only at the mouthpiece. A potential advantage of this is to allow separate control of airflow through each dose cartridge. It is also to be understood that a bypass conduit is also provided in some embodiments which is configured for use with a plurality of drug conduit tracts.

In some embodiments, a plurality of chambers (holders) 1520, 1530 are provided within a single tract of a drug conduit. Optionally, differential control of drug substance vaporization comprises differential heating of drug doses contained in each holder.

Figure 10A:
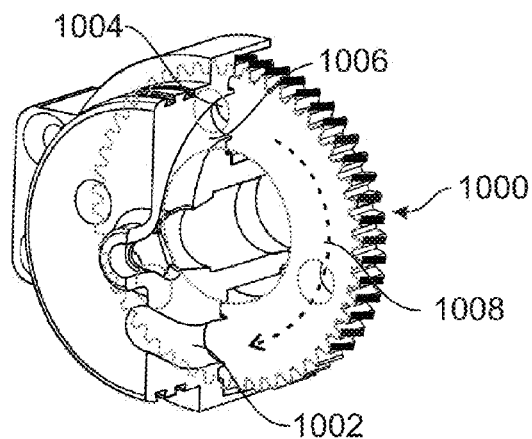
FIGS. 10A-10C are isometric, partially cross-sectional views of the mouthpiece during operating stages of the inhaler device, according to some embodiments.
Figure 10B:
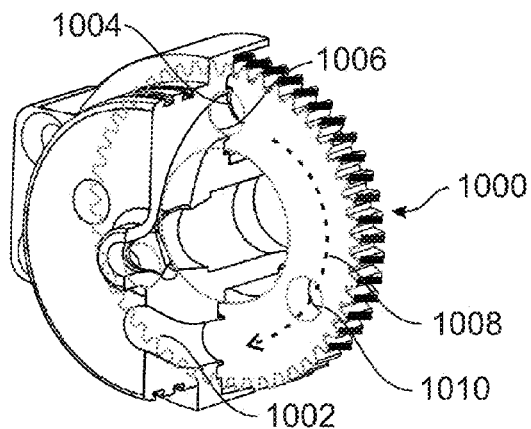
Figure 10C:
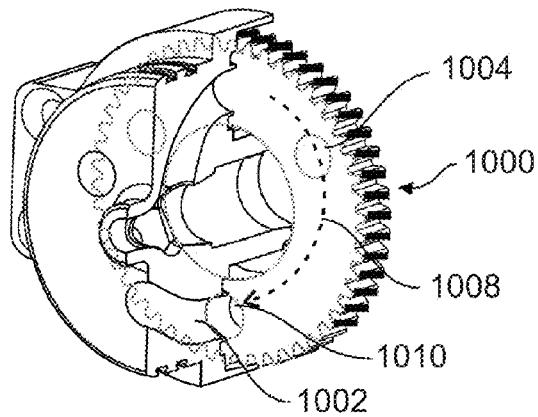

Reference is now made to FIGS. 10A-10C, which are isometric, partially cross-sectional views of the mouthpiece during operating stages of the inhaler device, according to some embodiments of the invention.

In FIG. 10A, disc 1000 is rotated to a position in which a distal opening of bypass conduit 1002 abuts against disc 1000, and the flow through bypass conduit 1002 is blocked. A partial overlap exists between valve opening 1004 and a distal opening of shunting conduit 1006, allowing limited air flow into shunting conduit.

In FIG. 10B, disc 1000 is rotated, for example, in the direction shown by arrow 1008, to a position in which bypass conduit 1002 is still obstructed, a full overlap exists between valve opening 1004 and shunting conduit 1006, allowing free flow into the shunting conduit 1006.

In FIG. 10C, disc 1000 is once again rotated in the direction of arrow 1008 to a position in which a valve opening 1010 overlaps with a distal opening of bypass conduit 1002, allowing flow through the bypass conduit, while obstructing flow through shunting conduit 1006.

Figure 11:
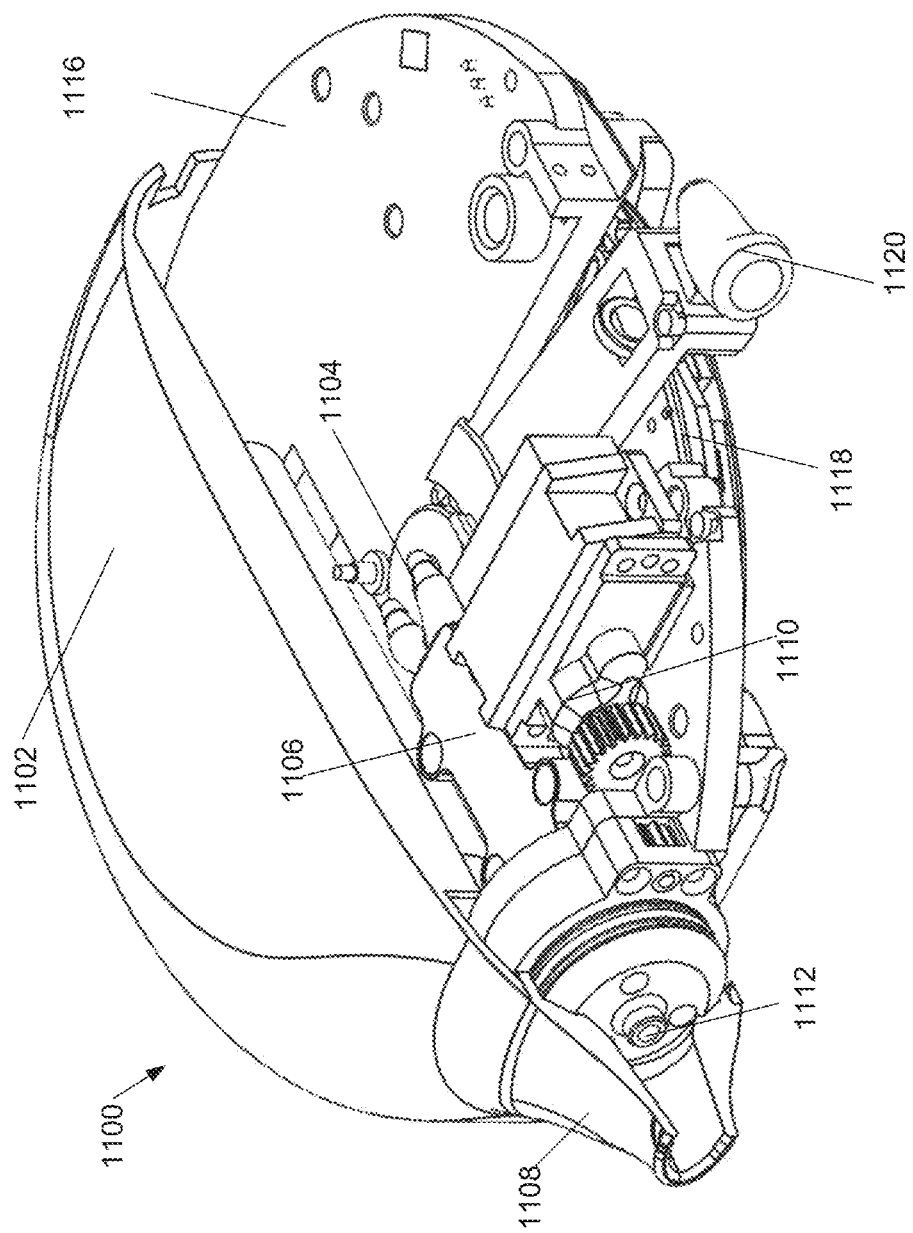
FIG. 11 shows a partial cross section view of an inhaler device, according to some embodiments.

Reference is now made to FIG. 11, which shows a partial cross section of an inhaler device, according to some embodiments of the invention.

In some embodiments, device 1100 is encased within an external housing 1102, optionally comprising a circular, disc-like shape. Alternatively, in some embodiments, housing 1102 comprises other shapes, such as a rectangular box shape, a cylindrical shape, and/or other shapes suitable for gripping by the user.

In the structure shown herein flow sensor 1104 is positioned at a distal end of drug conduit 1106. Drug conduit 1106 extends in a proximal direction up to mouthpiece 1108. A proximal opening 1112 of drug conduit 1106 is centralized with a proximal opening of mouthpiece 1108, which is to be engaged by the mouth of the user.

A valve disc (optionally configured as a cogwheel, encased within an internal housing in this Figure), configured for controlling flow through the conduits of the device, is operably coupled to a gear motor 1110. Optionally, gear motor 1110 is operated by a controller, located for example within a housing 1116.

In some embodiments, the device comprises a drug cartridge, for example shaped as a disc 1118 loaded with one or more drug dose units. Optionally, the controller is configured to actuate movement of the disc, for example prior to a use session and/or between use sessions.

In some embodiments, the device comprises a lever 1120 for manually loading or unloading a drug cartridge (as a disc 1118 in the shown example).

Figure 12:
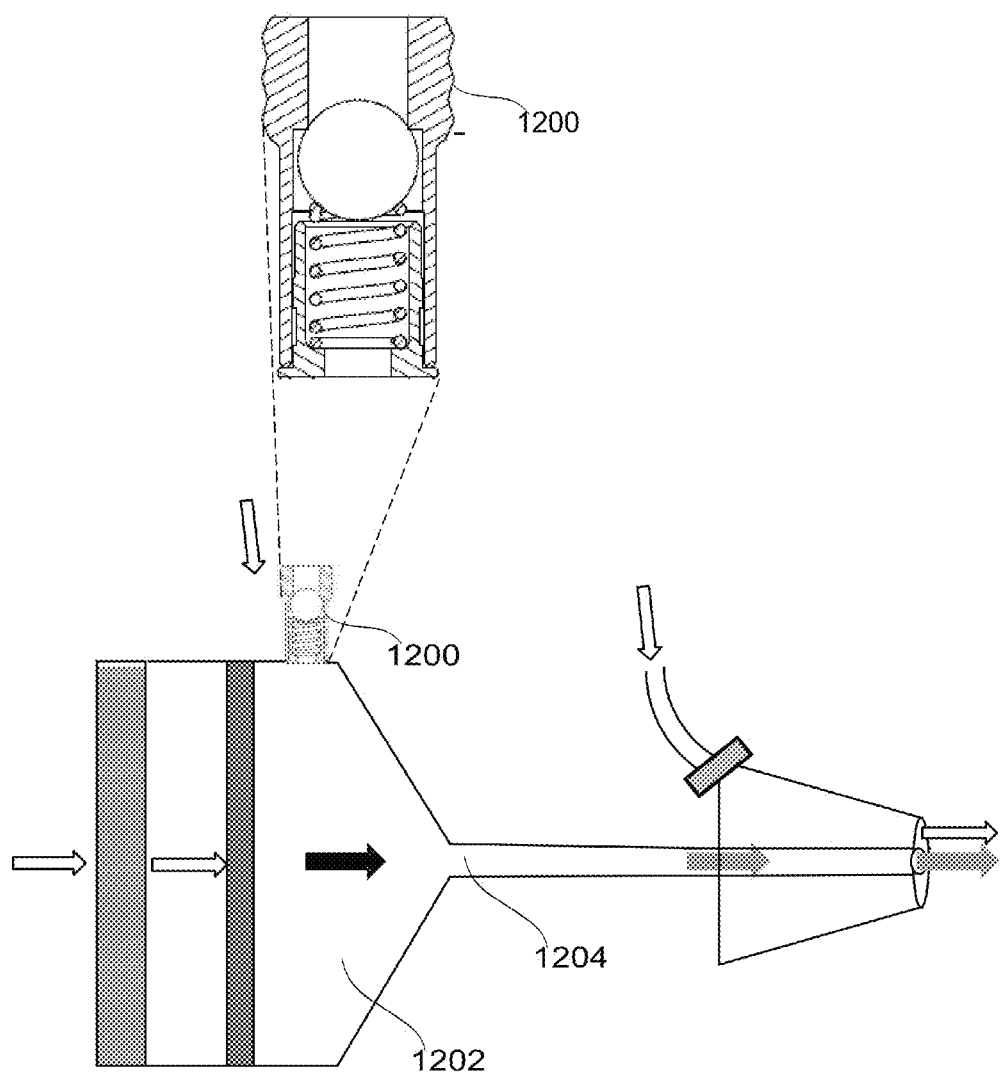
FIG. 12 is a schematic illustration of components of a mechanically operated flow control system, for example as incorporated within an inhaler device, according to some embodiments.
Figure 14:
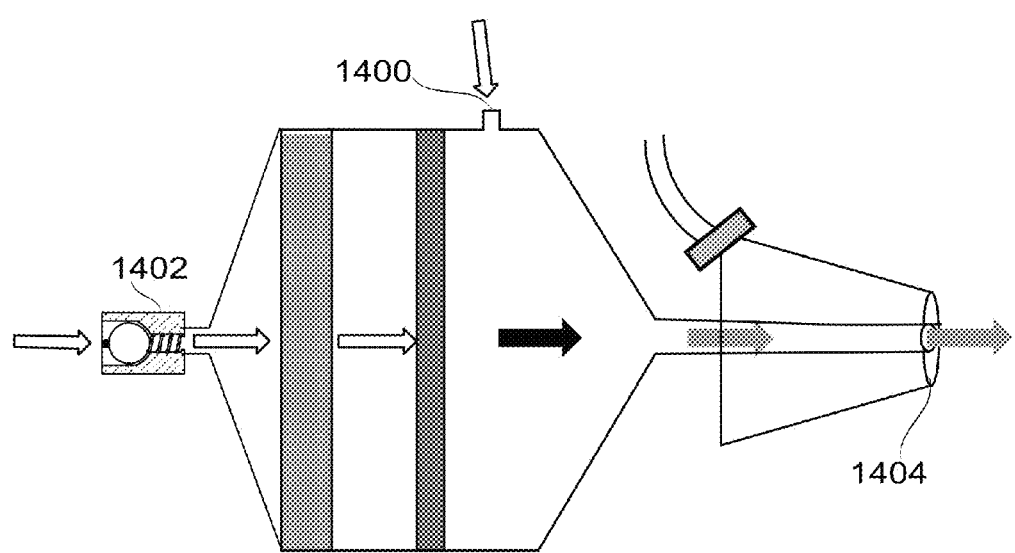
FIG. 14 is a schematic illustration of another mechanically operated flow control system, according to some embodiments.

Reference is now made to FIG. 12, which is a schematic illustration of components of a mechanically operated flow control system, for example as incorporated within an inhaler device, according to some embodiments. Reference is also made to FIG. 14, which is a schematic illustration of another mechanically operated flow control system, according to some embodiments.

In some embodiments, flow control is at least partially provided by a mechanical element, for example a check valve. Some embodiments do not involve electrical airflow control, such as by a controller and/or an air flow sensor, and are controlled and/or operated solely by purely mechanical elements, for example in response to pressure changes.

In this configuration, a check valve, for example a ball check valve 1200 (shown in an enlarged view as well), is positioned in communication with chamber 1202 (and/or with drug conduit 1204). Optionally, check valve 1200 allows shunting air flow into the inhaler device (to join the flow that passed through the drug dose) in response to pressure differences. In some embodiments, when a user inhales through the device, a pressure difference is created between chamber 1202 and the environment. Optionally, the pressure difference is large enough to cause valve 1200 to open and allow flow of ambient air into the device. Optionally, the extent of opening of check valve 1200 varies in response to a change in the pressure gradient, so that equilibrium is reached. For example, if the gradient increases (i.e. the pressure in the chamber decreases), the opening will expand to allow more flow to enter, thereby maintaining a constant pressure within the chamber.

In some embodiments, flow through the drug dose is at least partially resisted, for example by shaping and/or sizing the drug conduit and/or chamber to resist flow, to allow a pressure difference between the chamber and the environment to form.

In some embodiments, a normally open reverse check or flutter valve 1402 is provided in the drug conduit which is configured to partially close, or at least momentarily close (for example, flutter) as a rate of flow through it increases. In some embodiments, this increases resistance in the carrier airflow pathway, potentially allowing flow at a shunting conduit 1400 to increase, thereby resulting in a greater ratio of shunting to carrier airflow at mouthpiece 1404. Optionally, the normal ratio of intake flow resistances shunting conduit 1400 and at valve 1402 is set (for example, by size or shape) so that the majority of flow intake is through the extraction pathway until closure of valve 1402 occurs. Optionally, check valve 1200 is used in conjunction with valve 1402, so that both pathways are mechanically regulated.

Potentially, activation of one or both of valves 1200, 1402 also serves as feedback to a user (e.g., due to noise of valve operation) that a rate of inhalation is sufficient and/or excessive.

In some embodiments, maintaining a constant pressure within the chamber produces a constant flow rate through the drug dose, even if inner pressure differences (e.g. between the chamber and the drug conduit) vary as a result of the naturally varying inhalation flow rate of the patient. Optionally, the targeted flow profile is configured and/or estimated according to a geometry of the chamber and/or conduits.

In some embodiments, flow through the bypass conduit is controlled by a timed spring valve, for example opening in a set time after activation of the device, for example to allow rapid flow to the user.

As used herein with reference to quantity or value, the term "about" means "within±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. An inhaler device for delivery to an inhaling user of at least one drug substance emitted from a dose cartridge, the inhaler device comprising:
   a first conduit for conducting a carrier airflow to a proximal opening of a mouthpiece;
   a holder configured to position the dose cartridge at a dose cartridge position defined by the holder within the carrier airflow of the first conduit;
   a second conduit, pneumatically coupled to the first conduit, for conducting a shunting airflow to the mouthpiece without passing the shunting airflow through the dose cartridge position;
   at least one valve in at least one of the first and second conduits;
   wherein the at least one valve is operated by a valve controller to control a rate of carrier airflow in response to a negative pressure generated by the inhaling user via the mouthpiece;
   a third conduit configured to conduct bypass airflow to the mouthpiece through a path separated from the first and second conduits, wherein the bypass airflow through the third conduit is controlled by a bypass valve; and
   wherein a bypass valve controller is functionally connected to the bypass valve to control airflow through the third conduit, wherein the valve controller and/or bypass valve controller are configured to generate a pattern of airflow modulations for providing a signal to the inhaling user, the pattern including substantially reducing a total rate of airflow to the user for an intermediate period after a first period of airflow, and then opening at least the third conduit to rapidly increase the airflow to a rate or volume sufficient to be sensed by the inhaling user; the valve controller configured to time the pattern of airflow modulations at the end of a use session during which the user inhaled from the inhaler device to indicate to the user that delivery has been completed.

2. The inhaler device of claim 1, comprising at least one sensor positioned and configured for detecting at least one parameter indicating a rate of the carrier airflow.

3. The inhaler device of claim 2, wherein the at least one sensor comprises a pressure sensor positioned in the first conduit proximal to the dose cartridge position.

4. The inhaler device of claim 2, wherein the valve controller is configured to receive an indication of the rate of the carrier airflow from the at least one sensor, and to operate the at least one valve based on the indication of the rate of the carrier airflow and a target profile for the carrier airflow.

5. The inhaler device of claim 4, wherein the indication comprises a rate of the carrier airflow sensed while the second conduit is at least partially obstructed.

6. The inhaler device of claim 5, wherein the valve controller is configured to operate the at least one valve based on a difference between the target profile and the rate of the carrier airflow sensed while the second conduit is at least partially obstructed.

7. The inhaler device of claim 4, wherein the valve controller is configured to modify the target profile based on the received indication of the rate of carrier airflow.

8. The inhaler device of claim 4, wherein the target profile comprises a constant flow rate through the first conduit and the dose cartridge position for at least a certain period.

9. The inhaler device of claim 4, comprising a fan positioned to affect carrier airflow through the first conduit.

10. The inhaler device of claim 9, wherein a controller is configured to operate the fan to induce airflow based on the indication of the rate of carrier airflow from the at least one sensor and a target profile for the carrier airflow.

11. The inhaler device of claim 1, wherein the second conduit is connected to at least the first conduit at a junction between the dose cartridge position and the proximal opening of the mouthpiece, and the junction is configured to conduct airflow from the second conduit to circumferentially surround the carrier airflow.

12. The inhaler device of claim 1, wherein the substantial reduction in the total rate of airflow is to no more than 50% of the total rate of airflow during the first period of airflow.

13. The inhaler device of claim 1, comprising an electrode configured to apply an electric current to an electrically resistive heating element of the dose cartridge, when the dose cartridge is positioned by the holder.

14. The inhaler device of claim 13, wherein when the dose cartridge is positioned by the holder, the electrically resistive heating element of the dose cartridge is configured to heat material of the dose cartridge to vaporize the at least one drug substance from the material, wherein released vapors of the at least one drug substance flow into the first conduit and enter the carrier airflow.

15. The inhaler device of claim 13, comprising:

at least one sensor positioned and configured for detecting at least one parameter indicating a rate of the carrier airflow; and a controller configured to control heating of material of the dose cartridge, based on the at least one parameter indicating the rate of carrier airflow.

16. The inhaler device of claim 15, comprising a temperature sensor positioned to detect a temperature of the dose cartridge, wherein the valve controller is configured to receive an indication of the temperature from the temperature sensor, and to operate the at least one valve based on the indication of the temperature.

17. The inhaler device of claim 16, wherein the valve controller operates the at least one valve to reduce the carrier airflow if the temperature falls below a threshold.

18. The inhaler device of claim 15, wherein the controller is configured to activate drug substance release when commencement of inhalation by the user is detected or when the rate of carrier airflow is above a threshold.

19. The inhaler device of claim 13, wherein the holder positions the dose cartridge within the first conduit such that the electrode is sealed from the carrier airflow.

20. The inhaler device of claim 1, wherein at least the valve controller is configured to communicate with one or more of a user interface and a physician interface.

21. The inhaler device of claim 1, wherein the at least one valve is operable by the valve controller based on one or more of: a flow rate of inhalation, a flow rate through the dose cartridge position, and a defined time from a detected or estimated event.

22. The inhaler device of claim 1, wherein the at least one valve comprises a valve positioned along the second conduit configured to at least partially close to limit a rate of shunting airflow, and thereby to affect the rate of carrier airflow.

23. The inhaler device of claim 1, wherein the valve controller is configured to adjust a degree of opening of the at least one valve based on at least one of the shunting airflow and the carrier airflow.

24. The inhaler device of claim 1, wherein the holder positions the dose cartridge such that at least 90% of the carrier airflow through the first conduit passes through the dose cartridge.

25. The inhaler device of claim 1, comprising a plurality of holders.

26. The inhaler device of claim 1, wherein the valve controller and/or bypass valve controller are configured to substantially reduce a total rate of airflow to the user for an intermediate period after a first period of airflow, and then open at least the third conduit during inhalation.

27. The inhaler device of claim 1, wherein the device is configured to provide the user with an additional audible, visual and/or tactile indication that delivery has been completed.

28. The inhaler device of claim 1, wherein the pattern of airflow modulations includes reducing a total rate of airflow to the user to the extent of a full obstruction.

* * * * *

UNITED STATES PATENT AND TRADEMARK OFFICE
CERTIFICATE OF CORRECTION

PATENT NO.        : 9,993,602 B2
APPLICATION NO.   : 15/312647
DATED             : June 12, 2018
INVENTOR(S)       : Perry Davidson et al.

It is certified that error appears in the above-identified patent and that said Letters Patent is hereby corrected as shown below:

On the Title Page

Item (72) Inventors:
After "Binyamin SCHWARTZ, Sde Eliezer (IL)",
Insert the following:
-- Roee LIFSHITZ, Moshav Beit Hillel (IL) --

Signed and Sealed this
Third Day of September, 2024

Katherine Kelly Vidal
*Director of the United States Patent and Trademark Office*